(12) United States Patent
Eastman et al.

(10) Patent No.: US 11,493,512 B2
(45) Date of Patent: Nov. 8, 2022

(54) BIOMARKERS AND METHODS FOR MEASURING AND MONITORING AXIAL SPONDYLOARTHRITIS ACTIVITY

(71) Applicant: Laboratory Corporation of America Holdings, Burlington, NC (US)

(72) Inventors: Paul Scott Eastman, South San Francisco, CA (US); Eric Sasso, South San Francisco, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 517 days.

(21) Appl. No.: 15/373,669

(22) Filed: Dec. 9, 2016

(65) Prior Publication Data

US 2017/0097347 A1     Apr. 6, 2017

Related U.S. Application Data

(63) Continuation of application No. PCT/US2015/034945, filed on Jun. 9, 2015.

(60) Provisional application No. 62/078,667, filed on Nov. 12, 2014, provisional application No. 62/010,252, filed on Jun. 10, 2014.

(51) Int. Cl.
| | |
|---|---|
| *G01N 33/564* | (2006.01) |
| *G01N 33/68* | (2006.01) |
| *G16B 25/00* | (2019.01) |
| *G16B 20/00* | (2019.01) |
| *G16B 25/10* | (2019.01) |
| *G16B 20/20* | (2019.01) |
| *G16H 50/50* | (2018.01) |

(52) U.S. Cl.
CPC .......... *G01N 33/564* (2013.01); *G01N 33/68* (2013.01); *G16B 20/00* (2019.02); *G16B 20/20* (2019.02); *G16B 25/00* (2019.02); *G16B 25/10* (2019.02); *G16H 50/50* (2018.01); *G01N 2800/102* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 4,230,797 A | 10/1980 | Boguslaski et al. | |
| 4,233,402 A | 11/1980 | Maggio et al. | |
| 4,275,149 A | 6/1981 | Litman et al. | |
| 4,376,110 A | 3/1983 | David et al. | |
| 4,659,678 A | 4/1987 | Forrest et al. | |
| 4,727,022 A | 2/1988 | Skold et al. | |
| 5,018,067 A | 5/1991 | Mohlenbrock et al. | |
| 5,744,305 A | 4/1998 | Fodor et al. | |
| 8,058,013 B2 | 11/2011 | Karl et al. | |
| 2002/0038227 A1 | 3/2002 | Fey et al. | |
| 2004/0122296 A1 | 6/2004 | Hatlestad et al. | |
| 2004/0122297 A1 | 6/2004 | Stahmann et al. | |
| 2005/0142569 A1 | 6/2005 | Guild et al. | |
| 2006/0094056 A1 | 5/2006 | Chappell et al. | |
| 2006/0286586 A1 | 12/2006 | Drexhage et al. | |
| 2007/0172888 A1 | 7/2007 | Hallermayer et al. | |
| 2007/0172897 A1* | 7/2007 | Maksymowych | G01N 33/6887 435/7.9 |
| 2008/0026485 A1 | 1/2008 | Hueber et al. | |
| 2009/0017472 A1 | 1/2009 | Stuhlmuller et al. | |
| 2009/0114627 A1 | 5/2009 | Nakamura | |
| 2009/0142792 A1 | 6/2009 | Robinson et al. | |
| 2009/0270272 A1 | 10/2009 | Karl et al. | |
| 2011/0137851 A1 | 6/2011 | Cavet et al. | |
| 2011/0251099 A1 | 10/2011 | Visvanathan et al. | |
| 2011/0269633 A1 | 11/2011 | Bilello et al. | |
| 2012/0258883 A1 | 10/2012 | Chappell et al. | |
| 2013/0052665 A1 | 2/2013 | Ling et al. | |
| 2014/0005071 A1 | 1/2014 | Chappell et al. | |
| 2014/0142861 A1 | 5/2014 | Hagstrom et al. | |
| 2016/0245795 A1* | 8/2016 | Baudouin .......... | G01N 33/5023 |
| 2016/0356792 A1* | 12/2016 | Bilello ............... | G01N 33/6893 |

FOREIGN PATENT DOCUMENTS

| | | | |
|---|---|---|---|
| JP | 2007506100 | 3/2007 | |
| JP | 2008545960 | 12/2008 | |
| JP | 2009524807 | 7/2009 | |
| JP | 2010506147 | 2/2010 | |
| JP | 2011520095 | 7/2011 | |
| WO | 2004056456 | 7/2004 | |
| WO | 2004088309 | 10/2004 | |
| WO | 2005029091 | 3/2005 | |
| WO | 2006125973 | 11/2006 | |
| WO | 2007039280 | 4/2007 | |
| WO | 2007085411 | 8/2007 | |
| WO | 2007089303 | 8/2007 | |
| WO | 2008037420 | 4/2008 | |
| WO | 2009114627 | 9/2009 | |
| WO | 2012/061821 | * 5/2012 | |
| WO | 2012061821 | 5/2012 | |
| WO | 2013167727 | 11/2013 | |
| WO | 2014118550 | 8/2014 | |
| WO | 2015132241 | 9/2015 | |
| WO | 2015191423 | 12/2015 | |

OTHER PUBLICATIONS

Huang et al. Medline, PMID: 21703579, 2011.*
Lotz et al. Ann Rheum Dis, 2013, vol. 72, pp. 1756-1763.*
Ray et al. J Immunol., 2006, 177 (4) 2601-2609.*
Beukelman et al. 2011. 63:465-482 (Year: 2011).

(Continued)

*Primary Examiner* — Michael L Borin
(74) *Attorney, Agent, or Firm* — Kilpatrick Townsend & Stockton LLP

(57) ABSTRACT

Biomarkers useful for diagnosing and assessing inflammatory disease activity, for prediction of risk for progressive spinal and joint damage, in particular for axial spondyloarthritis (axSpA) and ankylosing spondylitis (AS), and for generating a dataset are provided, along with kits for measuring expression of the biomarkers. The invention also provides predictive models, based on the biomarkers, as well as computer systems, and software embodiments of the models for scoring and optionally classifying samples.

13 Claims, 14 Drawing Sheets

(56) References Cited

OTHER PUBLICATIONS

European Communication Response from Application No. 16852551.7, dated Oct. 31, 2018, 2 pages.
Jeffrey R. 2010. Medicine 38:167-171 (Year: 2010).
Petty et al. 2004. J. Rhematol. 31 :390-392 (Year: 2004).
Pisetsky et al. 2012. Best Pract Res. Clin. Rheumatol. 26:251-261 (Year: 2012).
Canadian Office Action Response from Application No. 2,777,800, dated Mar. 14, 2018, 52 pages.
European Communication from Application No. 10824227.2, dated Mar. 9, 2018, 9 pages.
European Communication Response from Application No. 10824227.2, dated May 10, 2018, 3 pages.
International Preliminary Report on Patentability from Application No. PCT/US2016/054323, dated Apr. 12, 2018, 13 pages.
Afuwape et al. (Histol. Histopathol. (2002) vol. 17, pp. 961-972.
Aletaha et al., Arth. Rheum. 2005, 52(9):2625-2636.
Baecklund et al., Arth. Rheum. 2006, 54(3):692-701.
Banerjee et al., Am. J. Cardiol. 2008, 101(8):1201-1205.
Benjamini and Hochberg. J. Royal Stat. Soc. B 1995 57(1):289-300.
Berk, "Statistical Learning from a Regression Perspective," Springer, 2008, p. 213.
Breedveld et al., Arth. Rheum. 2006, 54(1):26-37.
Breiman, Machine Learning 2001, 45(1):5-32.
Brown et al., Arth. Rheum. 2006, 54:3761-3773.
Brown et al., Arth. Rheum. 2008, 58(10):2958-2967.
Busquets-Perez et al., "Emerging drugs for axial spondyloarthritis including ankylosing spondlyitis", Expert Opinion on Emerging Drugs, vol. 18, No. 1, pp. 71-86 (2013).
Chan et al., "Evidence-Based Rheumatology", ed. M. Matucci Cerinic. Exp. Rheum. (2002), vol. 20, No. 4, pp. 443-444.
Chandran, "Soluble biomarkers may differentiate psoriasis from psoriatic arthritis", The Journal of Rheumatology, vol. 89, pp. 65-66 (2012).
Chinese First Office Action, Chinese Application No. 201080057651.4, dated Jun. 21, 2013, 14 pages.
Chinese Second Office Action, Chinese Application No. 201080057651.4, dated Jan. 13, 2014, 8 pages.
Churchman et al., Ann. Rheum. Dis'. 2009, 68:A1-A56, Abstract A77.
Coffman et al. Critical Reviews in Clinical Laboratory Sciences (2008) vol. 46, No. 6, pp. 531-562.
Cohen et al., Ann. Rheum. Dis'. 2007, 66:358-363.
Duurland et al., "Current developments in the use of biomarkers for juvenile idiopathic arthritis", Current Rheumatology Reports, vol. 16, No. 3, Article No. 406, pp. 1-6 (Epub. Jan. 21, 2014).
European Communication Response from Application No. 10824227.2, dated Oct. 26, 2015.
Extended European Search Report for Application No. 10824227.2, dated May 8, 2015.
Felson d.T. et al., "The American college of Rheumatology Preliminary Core Set of Disease Activity Measures for Rheumatoid Arthritis Clinical Trials", Arthritis & Rheumatism (1993), vol. 36, No. 6, pp. 729-740.
Felson d.T. et al., "The American College of Rheumatology: Preliminary Definition of Improvement in Rheumatoid Arthritis Clinical Trials", Arthritis & Rheumatism (1995), vol. 38, No. 6, pp. 727-735.
Fransen J. et al., "Validity of the Disease Activity Score in Undifferentiated Arthritis", Arthritis Care and Research (2010), vol. 62, No. 10, pp. 1392-1398.
Goekoop-Ruiterman et al., Ann. Rheum. Dis. 2009 (Epublication Jan. 20, 2009).
Goekoop-Ruiterman et al., Arth. Rheum. 2005, 52:3381-3390.
Goodson et al., Ann. Rheum. Dis. 2005, 64(11):1595-1601.
Gossec L. et al., "Prognostic Factors for Remission in Eady Rheumatoid Arthritis: A Multiparameter Prospective Study", Ann. Rheum. Dis. (2004), vol. 63, No. 6, pp. 675-680.
Green et al. (Rheumatology (2003) vol. 42, pp. 83-88).
Grigor C. et al., "Effect of a Treatment Strategy of Tight Control Rheumatoid Arthritis (the TICORA Study): A Single-Blind Randomised Controlled Trial", Lancet (2004), vol. 364, pp. 263-269.
Guler-Yuksel M. et al., "Changes in Hand and Generalised Bone Mineral Density in Patients with Recent-Onset Rheumatoid Arthritis", Ann. Rheum. Dis. (2009), vol. 68, pp. 330-336.
Hueber et al. (Arthritis & Rheumatism (2005) vol. 52, pp. 2645-2655).
International Preliminary Report on Patentability from Application No. PCT/US2010/052970, dated Dec. 16, 2010.
International Preliminary Report on Patentability from Application No. PCT/US2015/023302, dated Oct. 13, 2016.
International Preliminary Report on Patentability from Application No. PCT/US2015/034631, dated Dec. 22, 2016.
International Preliminary Report on Patentability from Application No. PCT/US2015/034945, dated Dec. 22, 2016.
International Search Report and Written Opinion from Application No. PCT/US2010/052970, dated Dec. 16, 2010.
International Search Report and Written Opinion from Application No. PCT/US2015/023302, dated Jun. 25, 2015.
International Search Report from Application No. PCT/US2015/034631, dated Aug. 28, 2015.
International Search Report from Application No. PCT/US2015/034945, dated Aug. 24, 2015.
International Search Report from Application No. PCT/US2016/054323, dated Dec. 8, 2016.
Japanese Office Action, Japanese Application No. 2012-534431, May 28, 2014, 14 pages.
Jarvis J. et al., "Gene-Expression Profiling: Time for Clinical Application", Lancet (2005), vol. 365, pp. 199-200.
Khan N.A, et al., "Duration of Morning Stiffness in the Assessment of Rheumatoid Arthritis Activity: A Questionable Issue", (Abstract) ACR/ARHP Scientific Meeting (2008), 1 page.
Kievit et al., Ann. Rheum. Dis'. 2008, 67(9):1229-1234.
Klooster et al. (Arthritis Research Ther. (2005) vol. 7, pp. R127-R138).
Kroot E.J.A. et al., "The Prognostic Value of Anti-Cyclic Citrullinated Peptide Antibody in Patients with Recent-Onset Rheumatoid Arthritis", Arthritis & Rheumatism (2000), vol. 43, No. 8, pp. 1831-1835.
Lipsky et al., iV. Engl. J. Med. 2000, 343:1594-1602.
Makinen et al., Ann. Rheum. Dis. 2005, 64(10):1410-1413.
Maksymowych et al., "Preliminary assessment of a multi-biomarker disease activity test for axial spondylorarthritis", In: 2014 American College of Rheumatology/The Association of Rheumatology Health Professionals (ACR/ARHP) Annual Meeting, Boston, MA, poster No. 2615 (Nov. 18, 2014).
Australian Office Action from Application No. 20110306593, dated May 1, 2015.
Australian Office Action from Application No. 20110306593, dated Dec. 2, 2014.
Australian Office Action Response from Application No. 2010306593, dated Feb. 19, 2015.
Canadian Office Action from Application No. 2,777,800, dated Nov. 7, 2016.
Canadian Office Action from Application No. 2,777,800, dated Sep. 14, 2017.
Canadian Office Action from Application No. 2,777,800, dated Dec. 21, 2015.
Canadian Office Action Response from Application No. 2,777,800, dated Jun. 16, 2016.
Canadian Office Action Response from Application No. 2,777,800, dated Apr. 28, 2017.
Centola et al., PLoS One, 2013, vol. 8, No. 4, pp. e606635.
Consolaro et al., Arthritis & Rheumatism, 2009, vol. 61, No. 5, pp. 658-666.
European Communication from Application No. 10824227.2, dated May 29, 2017.
European Communication Response from Application No. 10824227.2, dated Sep. 25, 2017.
European Communication Response from Application No. 15772723.1, dated Apr. 12, 2017.

(56) References Cited

OTHER PUBLICATIONS

European Communication Response from Application No. 15806913.8, dated Jun. 6, 2017.
Extended European Search Report for Application No. 15772723.1, dated Jul. 28, 2017.
International Search Report from Application No. PCT/US2016/054318, dated Jan. 13, 2017.
International Search Report from Application No. PCT/US2017/020181, dated Jun. 12, 2017.
Japanese Office Action from Japanese Application No. 2012-534431, dated Sep. 8, 2014.
Japanese Office Action Response from Japanese Application No. 2012-534431, dated Aug. 14, 2014.
Japanese Office Action Response from Japanese Application No. 2012-534431, dated Oct. 17, 2014.
Johansen et al.. Rheumatology, 1999, vol. 38, pp. 618-626.
Miller et al., Pediatric Rheumatology, 2011, vol. 9, No. 9, pp. 1-7.
Partial European Search Report for Application No. 15806913.8, dated Nov. 10, 2017.
Pedersen et al., Annals of the Rheumatic Diseases, 2011, vol. 70, No. 8, pp. 1375-1381.
Ringold et al., Annals of the Rheumatic Diseases, 2014, vol. 73, No. Suppl. 2, pp. 587.3-588.
Ringold et al., Arthritis & Rheumatology, 2014, vol. 66, pp. S10-S11.
Schierbeck et al., J. Rheumatol., 2013, vol. 40, pp. 1604-1613.
Shimizu et al., Cytokine, 2013, vol. 61, pp. 345-348.
Tilleman et al., Proteo, 2005, vol. 5, No. 8, pp. 2247-2257.
Mallya R.K. et al., "Correlation of Clinical Parameters of Disease Activity in Rheumatoid Arthritis with Serum Concentration of C-Reactive Protein and Erythrocyte Sedimentation Rate", The Journal of Rheumatology (1982), vol. 9, No. 2, pp. 224-228.
Morel et al. (The Journal of Biol. Chem. (2002) vol. 277, pp. 34679-34691.
Mottonen et al., Arth. Rheum. 2002, 46(4):894-898.
Nadareishvili Z. et al., "Cardiovascular, Rheumatologic, and Pharmacologic Predictors of Stroke in Patients with Rheumatoid Arthritis: A Nested Case-Controlled Study", Arthritis Rheum. (2008), vol. 59, No. 8, pp. 1090-1096.
Partial European Search Report for Application No. 10824227.2, dated Jan. 12, 2015.
Pearson T.A. et al., "Markers of Inflammation and Cardiovascular Disease: Application to Clinical and Public Health Practice: A Statement for Healthcare Professionals From the Centers for Disease Control and Prevention and the American Heart Association", Circulation, 2003, pp. 499-511.
Pettit et al., Am. J. Pathol. 2001, 159:1689-99.
Pincus T. et al., "Relative Versus Absolute Goals of Therapies for RA: ACR 20 or ACR 50 Responses Versus Target Values for "Near Remission" of DAS or Single Measures", Clin. Exp. Rheum. (2004), vol. 22, Suppl. 35, pp. S50-S56.
Plant M.J. et al., "Relationship Between Time-Integrated C-Reactive Protein Levels and Radiologic Progression in Patients with Rheumatoid Arthritis", Arthritis & Rheumatism (2000), vol. 43, No. 7, pp. 1473-1477.
Prakken et al., "Juvenile idopathic arthritis", The Lancet, vol. 377, No. 9783, pp. 2138-2149 (2011).
Prevoo M.L.L. et al., "Modified Disease Activity Scores That Include Twenty-Eight-Joint Counts", Arthritis & Rheumatism (1995), vol. 38, No. 1, pp. 44-48.
Ranganath et al., J. Rheum. 2008, 35:1966-1971.
Ridker P.M. et al., "C-Reactive Protein and Other Markers of Inflammation in the Prediction of Cardiovascular Disease in Women", The New England Journal of Medicine (2000), vol. 342, No. 12, pp. 836-843.
Ritchlin, "Biomarker development in psoriatic arthritis", The Journal of Rheumatology, Vo. 89, pp. 57-60 (2012).
Senolt et al. (Ann. Rheum. Dis. (2007) vol. 66, pp. 458-463.
Smolen et al. (Arthritis Research Therapy (2008) vol. 10, pp. 208-219; Published May 2008).
Smolen et al., Arth. Rheum. 2005, 52(4): 1020-30.
Smolen S. et al., "A Simplified Disease Activity Index for Rheumatoid Arthritis for Use in Clinical Practice", Rheumatology (Oxford, 2003), vol. 42, pp. 244 257.
Sokka et al., Clin. Exp. Rheum. 2006, 24(Suppl. 43):S74-S76.
Stucki G. et al., "A Self-Administered Rheumatoid Arthritis Disease Activity Index (RADA) for Epidemiologic Research", Arthritis & Rheumatism (1995), vol. 38, No. 6, pp. 795-798.
Taylor et al., Arth. Rheum. 2004, 50(4):1107-1116.
Tibshirani, J. Royal Stat. Soc., series B 1996, 58(1):267-288.
Toonen et al. "Gene expression profiling in rheumatoid arthritis: Current concepts and future directions", Annals of the Rheumatic Diseases Dec. 2008 GB, vol. 67, No. 12, Dec. 2008, pp. 1663-1669.
Van den Berg et al., Arth. Rheum. 2005, 52:995-999.
Van Den Broek et al. "The evolution of biomarkers in rheumatoid arthritis: From clinical research to clinical care", Expert Opinion on Biological Therapy Nov. 2008 GB, vol. 8. No. 11, Nov. 2008, pp. 1773-1785.
Van der Heijde et al., Ann. Rheum. Dis'. 1990, 49(11):916-920.
Van Gestel A.M. et al., "Validation of Rheumatoid Arthritis Improvement Criteria That Include Simplified Joint Counts", Arthritis & Rheumatism (1998), vol. 41, No. 10, pp. 1845-1850.
Van Leeuwen et al., Br. J. Rheum. 1993, 32(suppl.):9-13.
Van Tuyl et al., Ann. Rheum. Dis'. 2008, 67:1574-1577.
Vasan, Circulation 2006, 113(19):2335-2362.
Verstappen S.M.M. et al., "Intensive Treatment with Methotrexate in Early Rheumatoid Arthritis: Aiming for Remission. Computer Assisted Management in Early Rheumatoid Arthritis (CAMERA, an Open-Label trategy Trial)", Ann. Rheum. Dis. (2007), vol. 66, pp. 1443-1449.
Visser, H. et al., "How to Diagnose Rheumatoid Arthritis Early: A Prediction Model for Persistent (Erosive) Arthritis," Arthritis & Rheumatism, Feb. 2002, pp. 357-365, vol. 46, Issue 2. May be Retrieved at <URL:http://onlinelibrary.wiley.com/doi/1 0.1 002/art.1 0117/pdf.
Visvanathan et al., "Inflammatory biomarkers, disease activity and spinal disease measures in patients with ankylosing spondylitis after treatment with infliximab", Annals of the Rhuematic Diseases, vol. 67, Issue 4, pp. 511-517 (2008).
Weinblatt et al., N. Engl. J. Med. 1999, 340:253-259.
Wells, G. et al., "Validation of the 28-Joint Disease Activity Score (DAS28) and European League Against Rheumatism Response Criteria Based on C-Reactive Protein Against Disease Progression in Patients with Rheumatoid Arthritis, and Comparison with the DAS28 Based on Erythrocyte Sedimentation Rate," Ann. Rheum. Dis., 2008, Published Online First May 19, 2008, pp. 954-960, vol. 68. May be Retrieved at <URL:http://ard.bmi.com/contenU68/6/954full.pdf+html>.
Wisiowska et al. (Rheumatol. International (2007) vol. 27, pp. 947-954).
Wolfe F., "Comparative Usefulness of C-Reactive Protein and Erythrocyte Sedimentation Rate in Patients with Rheumatoid Arthritis", The Journal of Rheumatology (1997), vol. 24, No. 8, pp. 1477-1485.
Wolfe F.,"A Reappraisal of HAQ Disability in Rheumatoid Arthritis", Arthritis & Rheumatism (2000), vol. 43, No. 12, pp. 2751-2761.
Zatarain and V. Strand, Nat. Clin. Pract. Rheum. 2006, 2(11):611-618 (Review).
Zou, J. Royal Stat. Soc., series B 2005, 67(2):301-320.

* cited by examiner

| Biomarker | ASDAS-ESR | | ASDAS-CRP | | mSASSS | |
|---|---|---|---|---|---|---|
| | Slope | R | Slope | R | Slope | R |
| SAA | 0.36 | 0.59 | 0.35 | 0.64 | 0.01 | 0.36 |
| CRP | 0.44 | 0.66 | 0.43 | 0.77 | 0.01 | 0.35 |
| IL-6 | 0.17 | 0.57 | 0.30 | 0.55 | 0.01 | 0.41 |
| TNF-RI | 0.04 | 0.44 | 0.29 | 0.54 | 0.00 | 0.50 |
| MMP1 | 0.15 | 0.39 | 0.12 | 0.51 | 0.01 | 0.38 |
| MMP3 | 0.06 | 0.30 | 0.06 | 0.39 | 0.00 | 0.32 |
| YKL-40 | 0.11 | 0.45 | 0.11 | 0.51 | 0.01 | 0.41 |
| Leptin | -0.02 | 0.06 | -0.04 | 0.12 | 0.00 | 0.12 |
| Resistin | 0.06 | 0.35 | 0.06 | 0.40 | 0.00 | 0.11 |
| EGF | 0.05 | 0.18 | 0.04 | 0.15 | 0.00 | 0.20 |
| VEGF | 0.10 | 0.43 | 0.07 | 0.32 | 0.00 | 0.11 |
| VCAM-1 | 0.02 | 0.21 | 0.03 | 0.36 | 0.00 | 0.26 |
| IL8 | 0.05 | 0.17 | 0.04 | 0.14 | 0.01 | 0.36 |
| ICAM-1 | 0.04 | 0.44 | 0.04 | 0.53 | 0.00 | 0.25 |
| IL-6R | 0.00 | 0.04 | -0.01 | 0.08 | 0.00 | 0.05 |
| MDC | 0.06 | 0.49 | 0.05 | 0.49 | 0.00 | 0.00 |

Figure 3

| Biomarker | ASDAS-ESR | ASDAS-CRP | mSASSS |
|---|---|---|---|
| CRP | 0.66 | 0.64 | 0.36 |
| SAA | 0.59 | 0.77 | 0.35 |
| IL-6 | 0.57 | 0.55 | 0.41 |
| MDC | 0.49 | 0.54 | 0.50 |
| YKL-40 | 0.45 | 0.51 | 0.38 |
| TNF-RI | 0.44 | 0.39 | 0.32 |
| ICAM-1 | 0.44 | 0.51 | 0.41 |
| VEGF | 0.43 | 0.12 | 0.12 |
| MMP1 | 0.39 | 0.40 | 0.11 |
| Resistin | 0.35 | 0.15 | 0.20 |
| MMP3 | 0.30 | 0.32 | 0.11 |
| VCAM-1 | 0.21 | 0.36 | 0.26 |
| EGF | 0.18 | 0.14 | 0.36 |
| IL8 | 0.17 | 0.53 | 0.25 |
| Leptin | 0.06 | 0.08 | 0.05 |
| IL-6R | 0.04 | 0.49 | 0.00 |

Figure 4

| BIOMARKER (log10 pg/mL) | ASDAS-ESR (Clinical) | ASDAS-CRP (Clinical) | mSASSS | BASDAI | BASFI |
|---|---|---|---|---|---|
| CRP | 0.69 | 0.77 | 0.35 | 0.41 | 0.52 |
| Haptoglobin | 0.59 | 0.59 | 0.26 | 0.34 | 0.51 |
| IL-6 | 0.57 | 0.55 | 0.41 | 0.27 | 0.40 |
| SAA | 0.56 | 0.64 | 0.36 | 0.26 | 0.40 |
| MMP1 | 0.51 | 0.46 | 0.38 | 0.29 | 0.23 |
| MDC | 0.49 | 0.50 | 0.00 | 0.46 | 0.51 |
| Calprotectin | 0.48 | 0.52 | 0.30 | 0.41 | 0.42 |
| YKL-40 | 0.45 | 0.51 | 0.41 | 0.28 | 0.33 |
| TNF-RI | 0.44 | 0.54 | 0.50 | 0.29 | 0.37 |
| ICAM-1 | 0.44 | 0.53 | 0.25 | 0.25 | 0.36 |
| VEGF | 0.43 | 0.32 | 0.11 | 0.32 | 0.32 |
| Resistin | 0.35 | 0.40 | 0.11 | 0.21 | 0.16 |
| ERAP1 | 0.33 | 0.44 | 0.27 | 0.27 | 0.43 |
| DKK1 | 0.32 | 0.27 | 0.05 | 0.16 | 0.12 |
| C3a | 0.30 | 0.36 | 0.17 | 0.31 | 0.39 |
| MMP3 | 0.30 | 0.39 | 0.32 | 0.23 | 0.28 |
| OPG | 0.28 | 0.27 | 0.39 | 0.00 | 0.19 |
| BAP | 0.27 | 0.34 | 0.40 | 0.08 | 0.17 |
| VCAM-1 | 0.21 | 0.36 | 0.26 | 0.16 | 0.13 |
| S100A12 | 0.19 | 0.26 | -0.02 | 0.22 | 0.15 |
| EGF | 0.18 | 0.15 | 0.20 | 0.21 | 0.36 |
| IL8 | 0.17 | 0.14 | 0.36 | 0.05 | 0.16 |
| Adiponectin | 0.06 | -0.09 | 0.26 | -0.14 | -0.13 |
| Sclerostin | 0.04 | 0.01 | 0.03 | -0.05 | 0.05 |
| IL-6R | -0.04 | -0.08 | 0.05 | -0.11 | -0.03 |
| Leptin | -0.06 | -0.12 | -0.12 | -0.04 | -0.05 |
| RANKL | -0.07 | -0.17 | 0.02 | -0.16 | -0.01 |
| MBDA | 0.63 | 0.68 | 0.39 | 0.30 | 0.40 |

Figure 10

BIOMARKERS AND METHODS FOR MEASURING AND MONITORING AXIAL SPONDYLOARTHRITIS ACTIVITY

RELATED APPLICATIONS

The application is related to and claims the benefit of International Application Serial No. PCT/US15/034945, filed Jun. 9, 2015. The present application and International Serial No. PCT/US15/034945 are related to and claim the priority benefit to U.S. provisional application No. 62/010,252, filed Jun. 10, 2014, and 62/078,667, filed Nov. 12, 2014, the entire contents of which are hereby incorporated by reference.

BACKGROUND

Axial spondyloarthritis (axSpA) is a form of spondyloarthritis in which the predominant symptom is back pain, where radiographic sacroiliitis may or may not be present. If definite radiographic sacroiliitis is present on an X-ray, the disease can be sub-classified as AS. Ankylosing spondylitis (AS) is an inflammatory disease of the axial skeleton that can lead to bone erosions, new bone formation, and spinal ankylosis. AS primarily affects the spine and pelvis, but can also affect peripheral joints and nonarticular structures. Individuals having axSpA, but do not have AS, are classified as having non-radiographic (or pre-radiographic) axial spondyloarthritis (nr-axSpA). Individuals with nr-axSpA may nonetheless exhibit AS symptoms such as inflammatory back pain, positive MRIs for inflammation around the sacroiliac joints, HLA-B27 positivity, enthesitis, uveitis, etc.

Tumor necrosis factor (TNF) is an important inflammatory mediator in axSpA and AS, as evidenced by the effectiveness of anti-TNF therapies in AS patients. However, the role of TNF in AS bone pathology is less well understand than for rheumatoid arthritis (RA) (Machado et al. *Annals of the rheumatic diseases* 69:1495-70 (2010)). The various biological processes of AS can be reflected in levels of circulating biochemical markers of inflammation (Appel et al., *Arthritis research & therapy* 10:R125 (2008); Visvanathan et al., *Annals of the rheumatic diseases* 67:511-7 (2008); Wagner et al. *Annals of the rheumatic diseases* 71:674-80 (2012)), angiogenesis (Appel (2008); Visvanathan (2008)), cartilage damage (Appel (2008); Vandooren et al., *Arthritis and rheumatism* 50:2942-53 (2004); Pedersen et al. *Annals of the rheumatic diseases* 70:1375-81 (2011)), and bone turnover (Appel (2008); Wagner (2012); Pederson (2011); Visvanathan (2008); Carter et al., *Ther Adv Musculoskel Dis.* 4:293-299 (2012)).

Even with the availability of anti-TNF therapy for axSpA or AS, substantial disease activity persists in many patients (Arends et al., *Arthritis research & therapy* 13:R94 (2011); Braun et al., *Annals of the rheumatic diseases* 71:661-7 (2012); Rudwaleit et al., *Annals of the rheumatic diseases* 63:665-70 (2004); Sieper et al., *Annals of the rheumatic diseases* 71:700-6 (2012)). Recommendations have been developed for the management of axSpA and/or AS, which include patient history (e.g., questionnaires), clinical parameters, laboratory tests, and imaging (Braun et al., *Annals of the rheumatic diseases* 70:896-904 (2011)). Additionally, several measures of disease activity have been developed (Zochling, J., *Arthritis care & research* 63 Suppl 11:S47-58 (2011)), including the Ankylosing Spondylitis Disease Activity Score (ASDAS) (Lukas et al., Annals of the rheumatic diseases 68:18-24 (2009); Machado et al., J. rheumatology 38: 1502-6 (2011)). As many as 2.7 million adults in the United States may be affected with axSpA. However, assessing axSpA or AS can be clinically challenging because of the subjective nature of the current tools used to assess axSpA and AS, and the corresponding need for sophisticated imaging to resolve clinical uncertainties. Although spinal inflammation attributable to axSpA or AS can be demonstrated by MRI, a direct link between clinical disease activity, spinal inflammation, and osteoproliferative changes has not been established. Moreover, it is difficult to determine how rapidly any therapeutic benefit becomes detectable by MRI.

Accurate, ongoing evaluation of disease activity is critical for optimally managing axSpA or AS, to minimize the damage to the spine and sacroiliac joints, and long-term functional disability that can result from persistent active disease. To achieve the maximum therapeutic benefits for individual subjects, it is important to be able to specifically quantify and assess the subject's disease activity at any particular time, determine the effects of treatment on disease activity, and predict future outcomes. No existing single biomarker or multi-biomarker test produces results demonstrating a high association with level of axSpA or AS disease activity. The embodiments of the present teachings identify multiple serum biomarkers for the accurate clinical assessment of disease activity in subjects with chronic inflammatory disease, such as axSpA, along with methods of their use. The embodiments of the present invention further identify multiple serum biomarkers for the diagnosis of axSpA, and prediction of risk for progressive damage to the spine and sacroiliac joints.

SUMMARY

The present teachings relate to biomarkers associated with inflammatory disease, and with autoimmune disease, including axSpA, and methods of using the biomarkers to measure disease activity in a subject.

In an embodiment, a method for monitoring the presence or absence of axial spondyloarthritis (axSpA) disease activity in a subject, for diagnosing axSpA in a subject, or for predicting risk of progressive damage, is provided. The method comprises providing a test sample comprising a sample of bodily fluid taken from the subject, and determining sample concentrations for three or more biomarkers selected from a group comprising calprotectin (dimer of S100A8 and S100A9 protein subunits; MRP-8/14); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); interleukin 6 (IL6); interleukin 8 (IL8); interleukin 1, beta (IL1B); interleukin 6 receptor (IL6R); leptin (LEP); Macrophage-derived chemokine (MDC); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA). The method further comprises determining whether the sample concentration for each biomarker is statistically significantly greater than minimum diagnostic concentration of corresponding control biomarkers that are indicative of axSpA, and classifying disease activity of axSpA in the subject, or diagnosing axSpA in the subject, based at least in part on the determination of whether the sample concentrations for the biomarkers from the subject are statistically significantly greater than minimum diagnostic concentrations indicative of axSpA. In an embodiment, the biomarkers comprise VCAM-1, EGF, VEGF-A, IL-6, TNF-R1, MMP-1, MMP-3, YKL-40, Leptin, Resistin, SAA, and CRP. In an embodiment, the sample concentrations for the subject are predictive a clinical assessment. In an embodiment, the clinical assessment is selected from the group consisting of Ankylosing Spondylitis Disease Activity Score (ASDAS), the Stoke Ankylosing Spondylitis Spinal Score (SASSS); the modified Stoke Ankylosing Spondylitis Spinal Score (mSASSS); Ankylosing Spondylitis Quality of Life Scale (ASQOL); Bath Ankylosing Spondylitis Disease Activity Index (BASDAI), Bath Ankylosing Spondylitis Functional Index (BASFI), Bath Ankylosing Spondylitis Global Score (BAS-G), Bath Ankylosing Spondylitis Metrology Index (BASMI), Dougados Functional Index (DFI), Health Assessment Questionnaire for the Spondyloarthropathies (HAQ-S), Revised Leeds Disability Questionnaire (RLDQ), and MRI. In an embodiment, the subject has received a treatment for axSpA, and determining efficacy of the treatment based on a statistically significant difference between the sample concentrations from the subject and the sample concentrations of the control. In an embodiment, a report is prepared in a format that is capable of being disseminated to the subject or a caregiver of the subject that provides information allowing the subject or caregiver to make decisions based on the diagnosis. In an embodiment, the axSpA is nr-axSpA (non-radiographic axial spondyloarthritis) or ankylosing spondylitis (AS). In an embodiment, the progressive damage is damage to a spine or sacroiliac joint.

In another embodiment, a method for monitoring the presence or absence of axSpA disease activity in a subject, for diagnosing axSpA in a subject, or for predicting risk of progressive damage is provided. The method comprises determining a first dataset associated with samples from a population of individuals wherein said population is negative for axSpA, wherein said first dataset comprises quantitative data for three or more biomarkers selected from a group comprising calprotectin (dimer of S100A8 and S100A9 protein subunits; MRP-8/14); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); interleukin 6 (IL6); interleukin 8 (IL8); interleukin 1, beta (IL1B); interleukin 6 receptor (IL6R); leptin (LEP); Macrophage-derived chemokine (MDC); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA); determining a plurality of MBDA scores for the individuals in said population based on the first dataset. The method further comprises deriving an aggregate MBDA value for said population, determining a second dataset associate with a sample from said subject wherein said second dataset comprises the selected biomarkers, determining a MBDA score for said subject, comparing the aggregate MBDA value to the MBDA score for the subject, and determining disease activity of axSpA in the subject, or diagnosing axSpA in the subject, based at least in part on said comparison. In an embodiment, the biomarkers comprise VCAM-1, EGF, VEGF-A, IL-6, TNF-R1, MMP-1, MMP-3, YKL-40, Leptin, Resistin, SAA, and CRP. In an embodiment, the datasets are obtained by a method comprising obtaining said samples from said population and said sample from said subject wherein said samples comprise a plurality of analytes, contacting said samples with reagents, generating a plurality of complexes between said reagents with said plurality of analytes, and detecting said plurality of complexes to obtain said datasets wherein said datasets comprise quantitative data for said biomarkers. In an embodiment, the MBDA score for the subject is predictive of a clinical assessment. In an embodiment, the clinical assessment is selected from the group consisting of Ankylosing Spondylitis Disease Activity Score (ASDAS), the Stoke Ankylosing Spondylitis Spinal Score (SASSS); the modified Stoke Ankylosing Spondylitis Spinal Score (mSASSS); Ankylosing Spondylitis Quality of Life Scale (ASQOL); Bath Ankylosing Spondylitis Disease Activity Index (BASDAI), Bath Ankylosing Spondylitis Functional Index (BASFI), Bath Ankylosing Spondylitis Global Score (BAS-G), Bath Ankylosing Spondylitis Metrology Index (BASMI), Dougados Functional Index (DFI), Health Assessment Questionnaire for the Spondyloarthropathies (HAQ-S), Revised Leeds Disability Questionnaire (RLDQ), and MRI. In an embodiment, the method further comprises receiving a third dataset associated with a second sample obtained from said subject, wherein said sample obtained from said subject and said second sample are obtained from said subject at different times, determining a second MBDA score for said subject from said third dataset, and comparing said MBDA score and said second MBDA score for said subject to determine a change in said MBDA scores, wherein said change indicates a change in axSpA activity in said subject, or the presence of axSpA in the subject. In an embodiment a report is prepared in a format that is capable of being disseminated to the subject or a caregiver of the subject that provides information allowing the subject or caregiver to make decisions based on the diagnosis. In an embodiment, the subject has received a treatment for axSpA, and the method further comprises determining a second MBDA score for a second subject wherein said second subject is of the same species as said first subject and wherein said second subject has received treatment for axSpA, comparing said MBDA score of said subject to said second MBDA score, and determining a treatment efficacy for said first subject based on said score comparison. In an embodiment, the axSpA is nr-axSpA or AS. In an embodiment, the progressive damage is damage to a spine or sacroiliac joint.

In another embodiment, a computer-implemented method for scoring a sample is provided. The method comprises receiving a first dataset associated with a first sample obtained from a first subject, wherein said first dataset comprises quantitative data for three or more biomarkers selected from a group comprising calprotectin (dimer of S100A8 and S100A9 protein subunits; MRP-8/14); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); interleukin 6 (IL6); interleukin 8 (IL8); interleukin 1, beta (IL1B); interleukin 6 receptor (IL6R); leptin (LEP); Macrophage-derived chemokine (MDC); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA), and determining, by a computer processor, a first MBDA score from said first dataset using an interpretation function, wherein said first MBDA score provides a classification of disease activity of axSpA in the subject, a diagnosis of axSpA in the subject, or a prediction of risk of progressive damage. In an embodiment, the biomarkers comprise VCAM-1, EGF, VEGF-A, IL-6, TNF-R1, MMP-1, MMP-3, YKL-40, Leptin, Resistin, SAA, and CRP. In an embodiment, the method further comprises receiving a second dataset associated with a second sample obtained from said first subject, wherein said first sample and said second sample are obtained from said first subject at different times, determining a second MBDA score from said second dataset using said interpretation function, and comparing said first MBDA score and said second MBDA score to determine a change in said MBDA scores, wherein said change indicates a change in said inflammatory disease activity in said first subject, or a diagnosis of axSpA in the subject. In an embodiment, the datasets are obtained by a method comprising obtaining said samples for said population and said sample from said subject wherein said samples comprise a plurality of analytes, contacting said samples with reagents, generating a plurality of complexes between said reagents with said plurality of analytes, and detecting said plurality of complexes to obtain said datasets wherein said datasets comprise quantitative data for said biomarkers. In an embodiment, said MBDA score for the subject is predictive of a clinical assessment. In an embodiment, the clinical assessment is selected from the group consisting of Ankylosing Spondylitis Disease Activity Score (ASDAS), the Stoke Ankylosing Spondylitis Spinal Score (SASSS); the modified Stoke Ankylosing Spondylitis Spinal Score (mSASSS); Ankylosing Spondylitis Quality of Life Scale (ASQOL); Bath Ankylosing Spondylitis Disease Activity Index (BASDAI), Bath Ankylosing Spondylitis Functional Index (BASFI), Bath Ankylosing Spondylitis Global Score (BAS-G), Bath Ankylosing Spondylitis Metrology Index (BASMI), Dougados Functional Index (DFI), Health Assessment Questionnaire for the Spondyloarthropathies (HAQ-S), Revised Leeds Disability Questionnaire (RLDQ), and MRI. In an embodiment, a report is prepared in a format that is capable of being disseminated to the subject or a caregiver of the subject that provides information allowing the subject or caregiver to make decisions based on the diagnosis. In an embodiment, the axSpA is nr-axSpA or AS. In an embodiment, the progressive damage is damage to a spine or sacroiliac joint.

In another embodiment, a method of treating a subject is provided. The method comprises classifying disease activity of axSpA in the subject, diagnosing axSpA in the subject, or predicting risk of progressive damage, and selecting an axSpA therapeutic regimen based on a MBDA score. The method comprises classifying disease activity by providing a test sample comprising a sample of bodily fluid taken from the subject, and determining sample concentrations for three or more biomarkers selected from a group comprising calprotectin (dimer of S100A8 and S100A9 protein subunits; MRP-8/14); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); interleukin 6 (IL6); interleukin 8 (IL8); interleukin 1, beta (IL1B); interleukin 6 receptor (IL6R); leptin (LEP); Macrophage-derived chemokine (MDC); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA). Classification further comprises determining whether the sample concentration for each biomarker is statistically significantly greater than minimum diagnostic concentration of corresponding control biomarkers that are indicative of axSpA, and classifying disease activity of axSpA in the subject, or diagnosing axSpA in the subject, based at least in part on the determination of whether the sample concentrations for the biomarkers from the subject are statistically significantly greater than minimum diagnostic concentrations indicative of axSpA. In an embodiment, the method comprises providing said axSpA therapeutic regimen. In an embodiment, the method further comprises determining a response to the treatment based on said MBDA score. In an embodiment, the methods further comprise determining an axSpA treatment course based on the MBDA score. In an embodiment, the axSpA is nr-axSpA or AS. In an embodiment, the progressive damage is damage to a spine or sacroiliac joint.

In another, a method for generating quantitative data for a subject is provided. The method comprises performing at least one immunoassay on a first sample from the subject to generate a first dataset comprising the quantitative data, wherein the quantitative data represents at least three biomarkers, wherein the at least three biomarkers are selected from a group comprising calprotectin (dimer of S100A8 and S100A9 protein subunits; MRP-8/14); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); interleukin 6 (IL6); interleukin 8 (IL8); interleukin 1, beta (IL1B); interleukin 6 receptor (IL6R); leptin (LEP); Macrophage-derived chemokine (MDC); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA); and wherein the subject has axial spondyloarthritis (axSpA) or is suspected of having axSpA. In another embodiment, the biomarkers comprise VCAM-1, EGF, VEGF-A, IL-6, TNF-R1, MMP-1, MMP-3, YKL-40, Leptin, Resistin, SAA, and CRP. In another embodiment, performance of the at least one immunoassay comprises: obtaining the first sample, wherein the first sample comprises the biomarkers; contacting the first sample with a plurality of distinct reagents; generating a plurality of distinct complexes between the reagents and markers; and detecting the complexes to generate the data. In another embodiment, the at least one immunoassay comprises a multiplex assay. In another embodiment, the quantitative data are predictive of a clinical assessment. In another embodiment, the clinical assessment is selected from the group consisting of Ankylosing Spondylitis Disease Activity Score (ASDAS), the Stoke Ankylosing Spondylitis Spinal Score (SASSS); the modified Stoke Ankylosing Spondylitis Spinal Score (mSASSS); Ankylosing Spondylitis Quality of Life Scale (ASQOL); Bath Ankylosing Spondylitis Disease Activity Index (BASDAI), Bath Ankylosing Spondylitis Functional Index (BASFI), Bath Ankylosing Spondylitis Global Score (BAS-G), Bath Ankylosing Spondylitis Metrology Index (BASMI), Dougados Functional Index (DFI), Health Assessment Questionnaire for the Spondyloarthropathies (HAQ-S), Revised Leeds Disability Questionnaire (RLDQ), and MRI. In another embodiment, the axSpA is nr-axSpA (non-radiographic axial spondyloarthritis) or ankylosing spondylitis (AS).

BRIEF DESCRIPTION OF THE DRAWINGS

The skilled artisan will understand that the drawings, described below, are for illustration purposes only. The drawings are not intended to limit the scope of the present teachings in any way.

FIG. 3 illustrates individual biomarker comparisons with ASDAS-ESR, ASDAS-CRP, and mSASSS based on Pearson Correlation Coefficients.

FIG. 4 illustrates individual biomarker comparisons with ASDAS-ESR, ASDA-CRP, and mSASSS based on second algorithm.

FIG. 10 illustrates individual biomarker comparisons with ASDAS-ESR, ASDAS-CRP, mSASSS, BASDAI, and BASFI based on Pearson Correlation Coefficients.

DESCRIPTION OF VARIOUS EMBODIMENTS

Figure 1:
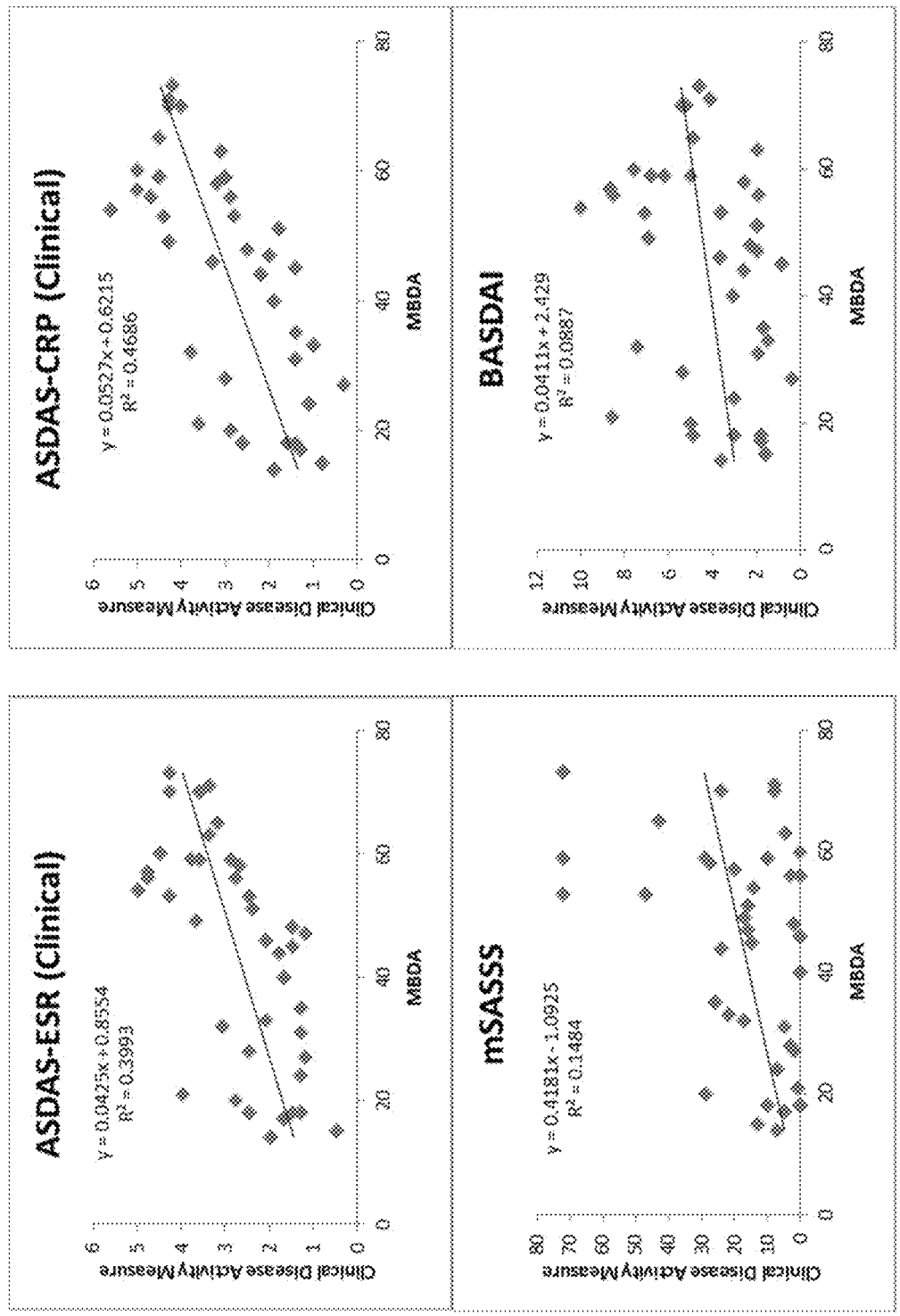
FIG. 1 illustrates the 12 biomarker VECTRA® DA panel MBDA comparisons with ASDAS-ESR (upper left), ASDAS-CRP (upper right), mSASSS (lower left), and BASDAI (lower right).

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to diagnostic applications of biomarkers associated with subjects having inflammatory and/or autoimmune diseases, such as for example axSpA, and that are useful in determining or assessing disease activity.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

Definitions

"Accuracy" refers to the degree that a measured or calculated value conforms to its actual value. "Accuracy" in clinical testing relates to the proportion of actual outcomes (true positives or true negatives, wherein a subject is correctly classified as having disease or as healthy/normal, respectively) versus incorrectly classified outcomes (false positives or false negatives, wherein a subject is incorrectly classified as having disease or as healthy/normal, respectively). Other terms related to "accuracy" (some being examples of measures of accuracy) can include, for example, "sensitivity," "specificity," "positive predictive value (PPV)," "the AUC," "negative predictive value (NPV)," "likelihood," and "odds ratio." "Analytical accuracy," in the context of the present teachings, refers to the repeatability and predictability of the measurement process. Analytical accuracy can be summarized in such measurements as, e.g., coefficients of variation (CV), and tests of concordance and calibration of the same samples or controls at different times or with different assessors, users, equipment, and/or reagents. See, e.g., R. Vasan, *Circulation* 2006, 113(19):2335-2362 for a summary of considerations in evaluating new biomarkers.

The term "algorithm" encompasses any formula, model, mathematical equation, algorithmic, analytical or programmed process, or statistical technique or classification analysis that takes one or more inputs or parameters, whether continuous or categorical, and produces an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, and neural networks trained on populations. Also of use in the context of biomarkers are linear and non-linear equations and statistical classification analyses to determine the relationship between (a) levels of biomarkers detected in a subject sample and (b) the level of the respective subject's disease activity.

"ALLMRK" in the present teachings refers to a specific group, panel, or set of biomarkers, as the term "biomarkers" is defined herein. Where the biomarkers of certain embodiments of the present teachings are proteins, the gene symbols and names used herein are to be understood to refer to the protein products of these genes, and the protein products of these genes are intended to include any protein isoforms of these genes, whether or not such isoform sequences are specifically described herein. Where the biomarkers are nucleic acids, the gene symbols and names used herein are to refer to the nucleic acids (DNA or RNA) of these genes, and the nucleic acids of these genes are intended to include any transcript variants of these genes, whether or not such transcript variants are specifically described herein. The ALLMRK group of the present teachings is the group of markers consisting of the following, where the name(s) or symbols in parentheses at the end of the marker name generally refers to the gene name, if known, or an alias: calprotectin (dimer of S100A8 and S100A9 protein subunits; MRP-8/14); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); interleukin 6 (IL6); interleukin 8 (IL8); interleukin 1, beta (IL1B); interleukin 6 receptor (IL6R); leptin (LEP); Macrophage-derived chemokine (MDC); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA)

The term "analyte" in the context of the present teachings can mean any substance to be measured, and can encompass biomarkers, markers, nucleic acids, electrolytes, metabolites, proteins, sugars, carbohydrates, fats, lipids, cytokines, chemokines, growth factors, proteins, peptides, nucleic acids, oligonucleotides, metabolites, mutations, variants, polymorphisms, modifications, fragments, subunits, degradation products and other elements. For simplicity, standard gene symbols may be used throughout to refer not only to genes but also gene products/proteins, rather than using the standard protein symbol; e.g., VEGFA as used herein can refer to the gene VEGFA and also the protein VEGFA. In general, hyphens are dropped from analyte names and symbols herein (IL-6=IL6).

To "analyze" includes determining a value or set of values associated with a sample by measurement of analyte levels in the sample. "Analyze" may further comprise comparing the levels against constituent levels in a sample or set of samples from the same subject or other subject(s). The biomarkers of the present teachings can be analyzed by any of various methods. Some such methods include but are not limited to: measuring serum protein or sugar or metabolite or other analyte level, measuring enzymatic activity, and measuring gene expression. Some such methods include analyzing a panel of biomarkers comprising at least some minimum number of test biomarkers disclosed herein as diagnostic, such test biomarkers optionally representing at least some minimum proportion of the total panel and/or contributing at least some minimum weight to the diagnostic test value/score derived from the measured levels of the panel.

The term "antibody" refers to any immunoglobulin-like molecule that reversibly binds to another with the required selectivity. Thus, the term includes any such molecule that is capable of selectively binding to a biomarker of the present teachings. The term includes an immunoglobulin molecule capable of binding an epitope present on an antigen. The term is intended to encompass not only intact immunoglobulin molecules, such as monoclonal and polyclonal antibodies, but also antibody isotypes, recombinant antibodies, bi-specific antibodies, humanized antibodies, chimeric antibodies, anti-idiopathic (anti-ID) antibodies, single-chain antibodies, Fab fragments, F(ab') fragments, fusion protein antibody fragments, immunoglobulin fragments, $F_v$ fragments, single chain $F_v$ fragments, and chimeras comprising an immunoglobulin sequence and any modifications of the foregoing that comprise an antigen recognition site of the required selectivity.

"Autoimmune disease" encompasses any disease, as defined herein, resulting from an immune response against substances and tissues normally present in the body. Examples of suspected or known autoimmune diseases include rheumatoid arthritis, juvenile idiopathic arthritis, seronegative spondyloarthropathies, axial spondyloarthritis (axSpA), non-radiographic axial spondyloarthritis (nr-axSpA) ankylosing spondylitis, psoriatic arthritis, antiphospholipid antibody syndrome, autoimmune hepatitis, Behçet's disease, bullous pemphigoid, coeliac disease, Crohn's disease, dermatomyositis, Goodpasture's syndrome, Graves' disease, Hashimoto's disease, idiopathic thrombocytopenic purpura, IgA nephropathy, juvenile idiopathic arthritis, Kawasaki disease, systemic lupus erythematosus, mixed connective tissue disease, multiple sclerosis, myasthenia gravis, polymyositis, primary biliary cirrhosis, psoriasis, scleroderma, Sjögren's syndrome, ulcerative colitis, vasculitis, Wegener's granulomatosis, temporal arteritis, Takayasu's arteritis, Henoch-Schonlein purpura, leucocytoclastic vasculitis, polyarteritis nodosa, Churg-Strauss Syndrome, and mixed cryoglobulinemic vasculitis.

"Ankylosing spondylitis" or "AS" is a form of axial spondyloarthritis wherein affected subjects have radiographic changes. AS affects joints in the spine and sacroiliac joint in the pelvis, which often leads to complete fusion of the spine.

"Axial spondyloarthritis" or "axSpA" is a form of spondyloarthritis in which the predominant symptom is back pain, where radiographic sacroiliitis may or may not be present. If definite radiographic sacroiliitis is present on an X-ray, the disease can be sub-classified as AS. A subset of axSpA is non-radiographic (or pre-radiographic) axial spondyloarthritis (nr-axSpA). Individuals having axSpA, but do not have AS, are classified as having nr-axSpA. Individuals with nr-axSpA may nonetheless exhibit AS symptoms such as inflammatory back pain, positive MRIs for inflammation around the sacroiliac joints, HLA-B27 positivity, enthesitis, uveitis, etc.).

"Biomarker," "biomarkers," "marker" or "markers" in the context of the present teachings encompasses, without limitation, cytokines, chemokines, growth factors, proteins, peptides, nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers and/or transcript variants. Biomarkers also encompass non-blood borne factors and non-analyte physiological markers of health status, and/or other factors or markers not measured from samples (e.g., biological samples such as bodily fluids), such as clinical parameters and traditional factors for clinical assessments. Biomarkers can also include any indices that are calculated and/or created mathematically. Biomarkers can also include combinations of any one or more of the foregoing measurements, including temporal trends and differences.

A "clinical assessment," or "clinical datapoint" or "clinical endpoint," in the context of the present teachings can refer to a measure of disease activity or severity. A clinical assessment can include a score, a value, or a set of values that can be obtained from evaluation of a sample (or population of samples) from a subject or subjects under determined conditions. A clinical assessment can also be a questionnaire completed by a subject. A clinical assessment can also be predicted by biomarkers and/or other parameters. One of skill in the art will recognize that the clinical assessment for axSpA or AS, as an example, can comprise, without limitation, one or more of the following: Ankylosing Spondylitis Disease Activity Score (ASDAS), the Stoke Ankylosing Spondylitis Spinal Score (SASSS); the modified Stoke Ankylosing Spondylitis Spinal Score (mSASSS); Ankylosing Spondylitis Quality of Life Scale (ASQOL); Bath Ankylosing Spondylitis Disease Activity Index (BASDAI), Bath Ankylosing Spondylitis Functional Index (BASFI), Bath Ankylosing Spondylitis Global Score (BAS-G), Bath Ankylosing Spondylitis Metrology Index (BASMI), Dougados Functional Index (DFI), Health Assessment Questionnaire for the Spondyloarthropathies (HAQ-S), Revised Leeds Disability Questionnaire (RLDQ), and MRI.

The term "clinical parameters" in the context of the present teachings encompasses all measures of the health status of a subject. A clinical parameter can be used to derive a clinical assessment of the subject's disease activity. Clinical parameters can include, without limitation: therapeutic regimen (including but not limited to therapies, whether conventional or biologics, steroids, etc.), damage to the spine and sacroiliac joints, radiographic changes and other imaging, gender/sex, age, race/ethnicity, disease duration, diastolic and systolic blood pressure, resting heart rate, height, weight, body-mass index, family history, CCP status (i.e., whether subject is positive or negative for anti-CCP antibody), CCP titer, RF status, RF titer, ESR, CRP titer, menopausal status, and whether a smoker/non-smoker.

"Clinical assessment" and "clinical parameter" are not mutually exclusive terms. There may be overlap in members of the two categories. For example, CRP titer can be used as a clinical assessment of disease activity; or, it can be used as a measure of the health status of a subject, and thus serve as a clinical parameter.

Figure 14:
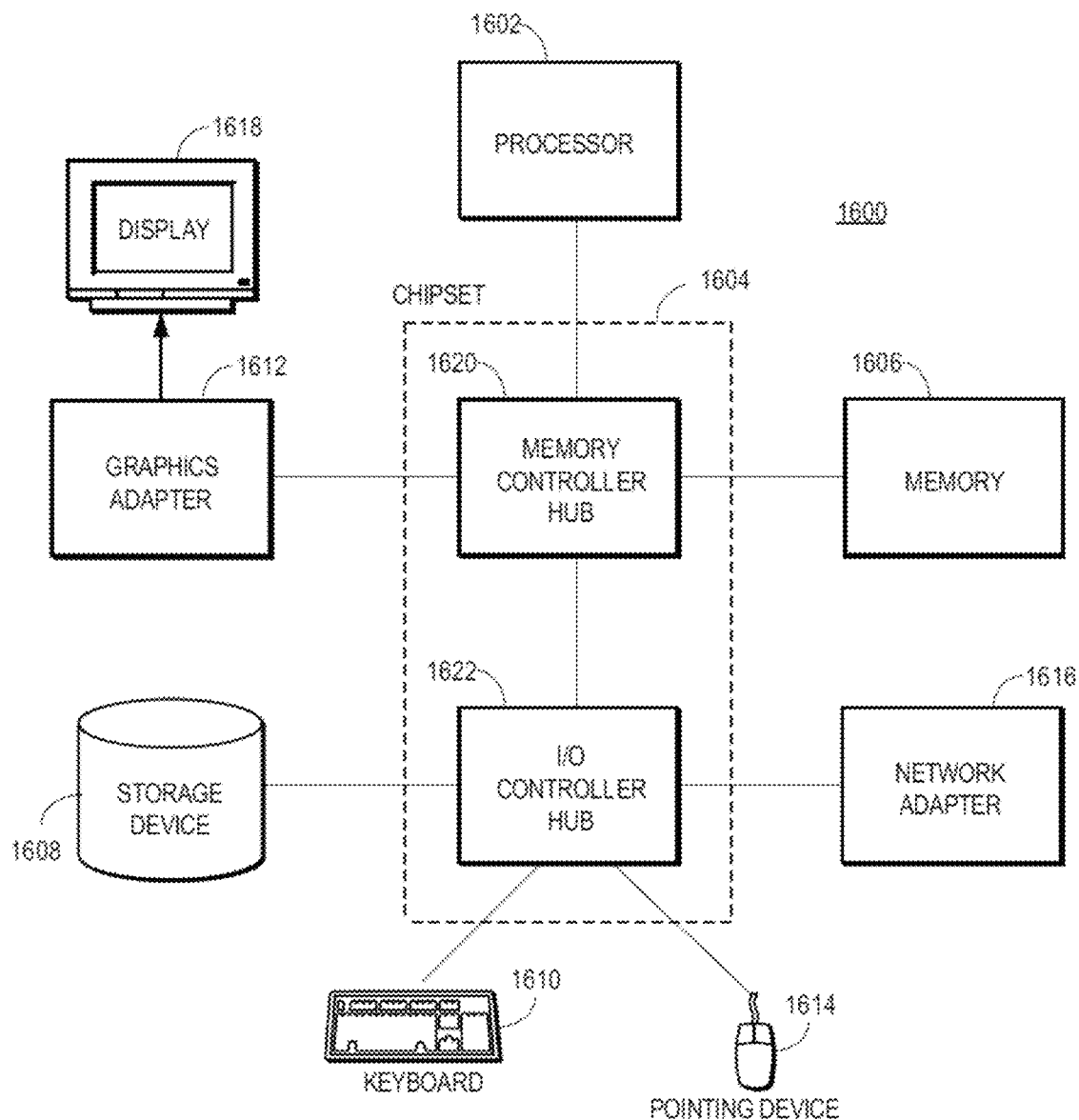
FIG. 14 is a high-level block diagram of a computer (1600). Illustrated are at least one processor (1602) coupled to a chipset (1604). Also coupled to the chipset (1604) are a memory (1606), a storage device (1608), a keyboard (1610), a graphics adapter (1612), a pointing device (1614), and a network adapter (1616). A display (1618) is coupled to the graphics adapter (1612). In one embodiment, the functionality of the chipset (1604) is provided by a memory controller hub 1620) and an I/O controller hub (1622). In another embodiment, the memory (1606) is coupled directly to the processor (1602) instead of the chipset (1604). The storage device 1608 is any device capable of holding data, like a hard drive, compact disk read-only memory (CD-ROM), DVD, or a solid-state memory device. The memory (1606) holds instructions and data used by the processor (1602). The pointing device (1614) may be a mouse, track ball, or other type of pointing device, and is used in combination with the keyboard (1610) to input data into the computer system (1600). The graphics adapter (1612) displays images and other information on the display (1618). The network adapter (1616) couples the computer system (1600) to a local or wide area network.

The term "computer" carries the meaning that is generally known in the art; that is, a machine for manipulating data according to a set of instructions. For illustration purposes only, FIG. 14 is a high-level block diagram of a computer (1600). A "computer" can have different and/or other components than those shown in FIG. 14. In addition, the computer 1600 can lack certain illustrated components. Moreover, the storage device (1608) can be local and/or remote from the computer (1600) (such as embodied within a storage area network (SAN)). A computer (1600) can be modified and adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device (1608), loaded into the memory (1606), and executed by the processor (1602). Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The term "cytokine" in the present teachings refers to any substance secreted by specific cells of the immune system that carries signals locally between cells and thus has an effect on other cells. The term "cytokines" encompasses "growth factors." "Chemokines" are also cytokines. They are a subset of cytokines that are able to induce chemotaxis in cells; thus, they are also known as "chemotactic cytokines."

Calprotectin is a heteropolymer, comprising two protein subunits of gene symbols S100A8 and S100A9. ICTP is the carboxyterminal telopeptide region of type I collagen, and is liberated during the degradation of mature type I collagen. Type I collagen is present as fibers in tissue; in bone, the type I collagen molecules are cross-linked. The ICTP peptide is immunochemically intact in blood. (For the type I collagen gene, see official symbol COL1A1, HUGO Gene Nomenclature Committee; also known as OI4; alpha 1 type I collagen; collagen alpha 1 chain type I; collagen of skin, tendon and bone, alpha-1 chain; and, pro-alpha-1 collagen type 1). Keratan sulfate (KS, or keratosulfate) is not the product of a discrete gene, but refers to any of several sulfated glycosaminoglycans. They are synthesized in the central nervous system, and are found especially in cartilage and bone. Keratan sulfates are large, highly hydrated molecules, which in joints can act as a cushion to absorb mechanical shock.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

In certain embodiments of the present teachings, a dataset of values is determined by measuring at least three biomarkers. This dataset is used by an interpretation function according to the present teachings to derive an MBDA score (see definition, "MBDA score," below), which provides a quantitative measure of inflammatory disease activity in a subject. In the context of axSpA or AS, the MBDA score thus derived from this dataset is also useful in predicting a clinical assessment, with a high degree of association, as is shown in the Examples below.

The term "diagnosis" or "diagnosing" as used herein refers to methods by which a determination can be made as to whether an individual is likely to be suffering from a given disease or condition. The skilled artisan often makes a diagnosis on the basis of one or more diagnostic indicators, e.g., a biomarker, the presence, absence, amount, or change in amount of which is indicative of the presence, severity, or absence of the condition. Other diagnostic indicators can include patient history; physical symptoms, e.g., unexplained weight loss, fever, fatigue, pains, or skin anomalies; phenotype; genotype; or environmental or heredity factors. A diagnosis of axSpA is based on the evaluation of the one or more diagnostic indicators that is indicative of axSpA, respectively. Each factor or symptom that is considered to be indicative for a diagnosis of axSpA does not need to be exclusively related to the disease; e.g., there may be differential diagnoses that can be inferred from a diagnostic factor or symptom. Similarly, there may be instances where a factor or symptom that is indicative of axSpA is present in an individual that does not have axSpA. The term "diagnosis" does not refer to the ability to predict the development of a condition with 100% accuracy, or even that the development of the condition is more likely to occur than not. Instead, the skilled artisan will understand that the term "diagnosis" refers to an increased probability that certain course or outcome will occur; that is, that a course or outcome is more likely to occur in a patient exhibiting a given characteristic, e.g., the presence or level of a diagnostic indicator, when compared to individuals not exhibiting the characteristic. Diagnostic methods can be used independently, or in combination with other diagnosing methods known in the art to determine whether a course or outcome is more likely to occur in a patient exhibiting a given characteristic. The term "monitor" or "monitoring" or "assessing" carries its common usage, and can refer to, inter alia, the observation of disease commencement or progression.

The term "disease" in the context of the present teachings encompasses any disorder, condition, sickness, ailment, etc. that manifests in, e.g., a disordered or incorrectly functioning organ, part, structure, or system of the body, and results from, e.g., genetic or developmental errors, infection, poisons, nutritional deficiency or imbalance, toxicity, or unfavorable environmental factors.

A therapy can be conventional or biologic. Examples of therapies that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intramuscular gold (IM gold), leflunomide (LEF), levofloxacin (LEV), and sulfasalazine (SSZ) certolizumab, JAK inhibitors, and apremilast. Examples of other conventional therapies include, but are not limited to, folinic acid, D-pencillamine, gold auranofin, gold aurothioglucose, gold thiomalate, cyclophosphamide, and chlorambucil. Examples of biologic therapies (or biologic drugs) include but are not limited to biological agents that target the tumor necrosis factor (TNF)-alpha molecules and the TNF inhibitors, such as infliximab, adalimumab, etanercept and golimumab. Other classes of biologic therapies include IL1 inhibitors such as anakinra, T-cell modulators such as abatacept, B-cell modulators such as rituximab, and IL6 inhibitors such as tocilizumab, and agents against IL12/23, IL-17, and IL-23.

"Inflammatory disease" in the context of the present teachings encompasses, without limitation, any disease, as defined herein, resulting from the biological response of vascular tissues to harmful stimuli, including but not limited to such stimuli as pathogens, damaged cells, irritants, antigens and, in the case of autoimmune disease, substances and tissues normally present in the body. Examples of inflammatory disease include axSpA, AS, RA, atherosclerosis, asthma, autoimmune diseases, chronic inflammation, chronic prostatitis, glomerulonephritis, hypersensitivities, inflammatory bowel diseases, pelvic inflammatory disease, reperfusion injury, transplant rejection, and vasculitis.

"Interpretation function," as used herein, means the transformation of a set of observed data into a meaningful determination of particular interest; e.g., an interpretation function may be a predictive model that is created by utilizing one or more statistical algorithms to transform a dataset of observed biomarker data into a meaningful determination of disease activity or the disease state of a subject.

A "minimum diagnostic concentration" is the concentration of an analyte or panel of analytes that defines the limit between the concentration range corresponding to normal disease-free function and the concentration reflective of an immune disorder.

"Measuring" or "measurement" or "detecting" in the context of the present teachings refers to determining the presence, absence, quantity, amount, or effective amount of a substance in a clinical or subject-derived sample, including the concentration levels of such substances, or evaluating the values or categorization of a subject's clinical parameters.

A "multi-biomarker disease activity index score," "MBDA score," "disease activity score," "score," or simply "MBDA," in the context of the present teachings, is a score that uses quantitative data to provide a quantitative measure of inflammatory disease activity or the state of inflammatory disease in a subject. A set of data from particularly selected biomarkers, such as from the disclosed set of biomarkers, is input into an interpretation function according to the present teachings to derive the MBDA score. The interpretation function, in some embodiments, can be created from predictive or multivariate modeling based on statistical algorithms. Input to the interpretation function can comprise the results of testing two or more of the disclosed set of biomarkers, alone or in combination with clinical parameters and/or clinical assessments, also described herein. In certain embodiments the score can be derived from a single constituent, parameter or assessment, while in other embodiments the score can be derived from multiple constituents, parameters and/or assessments. In certain embodiments the score can be derived from a single constituent, parameter or assessment, while in other embodiments the score can be derived from multiple constituents, parameters and/or assessments. In some embodiments of the present teachings, the MBDA score is a quantitative measure of autoimmune disease activity. In some embodiments, the MBDA score is a quantitative measure of axSpA disease activity. A "change in score" can refer to the absolute change in score, e.g. from one time point to the next, or the percent change in score, or the change in the score per unit time (e.g., the rate of score change). MBDA as used herein can refer to a VECTRA® DA-like score applied to axial spondyloarthritis.

"Performance" in the context of the present teachings relates to the quality and overall usefulness of, e.g., a model, algorithm, or diagnostic or prognostic test. Factors to be considered in model or test performance include, but are not limited to, the clinical and analytical accuracy of the test, use characteristics such as stability of reagents and various components, ease of use of the model or test, health or economic value, and relative costs of various reagents and components of the test.

A "population" is any grouping of subjects of like specified characteristics. The grouping could be according to, for example but without limitation, clinical parameters, clinical assessments, therapeutic regimen, disease status (e.g. with disease or healthy), level of disease activity, etc. In the context of using the MBDA score in comparing disease activity between populations, an aggregate value can be determined based on the observed MBDA scores of the subjects of a population; e.g., at particular time points in a longitudinal study. The aggregate value can be based on, e.g., any mathematical or statistical formula useful and known in the art for arriving at a meaningful aggregate value from a collection of individual data points; e.g., mean, median, median of the mean, etc.

A "predictive model," which term may be used synonymously herein with "multivariate model" or simply a "model," is a mathematical construct developed using a statistical algorithm or algorithms for classifying sets of data. The term "predicting" refers to generating a value for a data point without actually performing the clinical diagnostic procedures normally or otherwise required to produce that data point; "predicting" as used in this modeling context should not be understood solely to refer to the power of a model to predict a particular outcome. Predictive models can provide an interpretation function; e.g., a predictive model can be created by utilizing one or more statistical algorithms or methods to transform a dataset of observed data into a meaningful determination of disease activity or the disease state of a subject. See Calculation of the MBDA score for some examples of statistical tools useful in model development.

A "prognosis" is a prediction as to the likely outcome of a disease. Prognostic estimates are useful in, e.g., determining an appropriate therapeutic regimen for a subject.

A "quantitative dataset," as used in the present teachings, refers to the data derived from, e.g., detection and composite measurements of a plurality of biomarkers (e.g., two or more) in a subject sample. The quantitative dataset can be used in the identification, monitoring and treatment of disease states, and in characterizing the biological condition of a subject. It is possible that different biomarkers will be detected depending on the disease state or physiological condition of interest.

A "report," as used herein, refers to any written or electronic form of data, whether or not displayed, either in raw data form or analyzed as to its significance, including charts, graphs, plots, tables, or summary information manifesting the significance of the data as applied to a given medical or medical-related test.

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

"Statistically significant" in the context of the present teachings means an observed alteration is greater than what would be expected to occur by chance alone (e.g., a "false positive"). Statistical significance can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered highly significant (not random chance) at a p-value less than or equal to 0.05.

A "subject" in the context of the present teachings is generally a mammal. The subject can be a patient. The term "mammal" as used herein includes but is not limited to a human, non-human primate, dog, cat, mouse, rat, cow, horse, and pig. Mammals other than humans can be advantageously used as subjects that represent animal models of inflammation. A subject can be male or female. A subject can be one who has been previously diagnosed or identified as having an inflammatory disease. A subject can be one who has already undergone, or is undergoing, a therapeutic intervention for an inflammatory disease. A subject can also be one who has not been previously diagnosed as having an inflammatory disease; e.g., a subject can be one who exhibits one or more symptoms or risk factors for an inflammatory condition, or a subject who does not exhibit symptoms or risk factors for an inflammatory condition, or a subject who is asymptomatic for inflammatory disease.

A "therapeutic regimen," "therapy" or "therapeutic regimen" or "treatment(s)," as described herein, includes all clinical management of a subject and interventions, whether biological, chemical, physical, or a combination thereof, intended to sustain, ameliorate, improve, or otherwise alter the condition of a subject. These terms may be used synonymously herein. Treatments include but are not limited to administration of prophylactics or therapeutic compounds (including conventional and novel DMARDs, biologic DMARDs, non-steroidal anti-inflammatory drugs (NSAIDs) such as COX-2 selective inhibitors, and corticosteroids), exercise regimens, physical therapy, dietary modification and/or supplementation, bariatric surgical intervention, administration of pharmaceuticals and/or anti-inflammatories (prescription or over-the-counter), and any other treatments known in the art as efficacious in preventing, delaying the onset of, or ameliorating disease. A "response to treatment" includes a subject's response to any of the above-described treatments, whether biological, chemical, physical, or a combination of the foregoing. A "treatment course" relates to the dosage, duration, extent, etc. of a particular treatment or therapeutic regimen.

Figure 12:
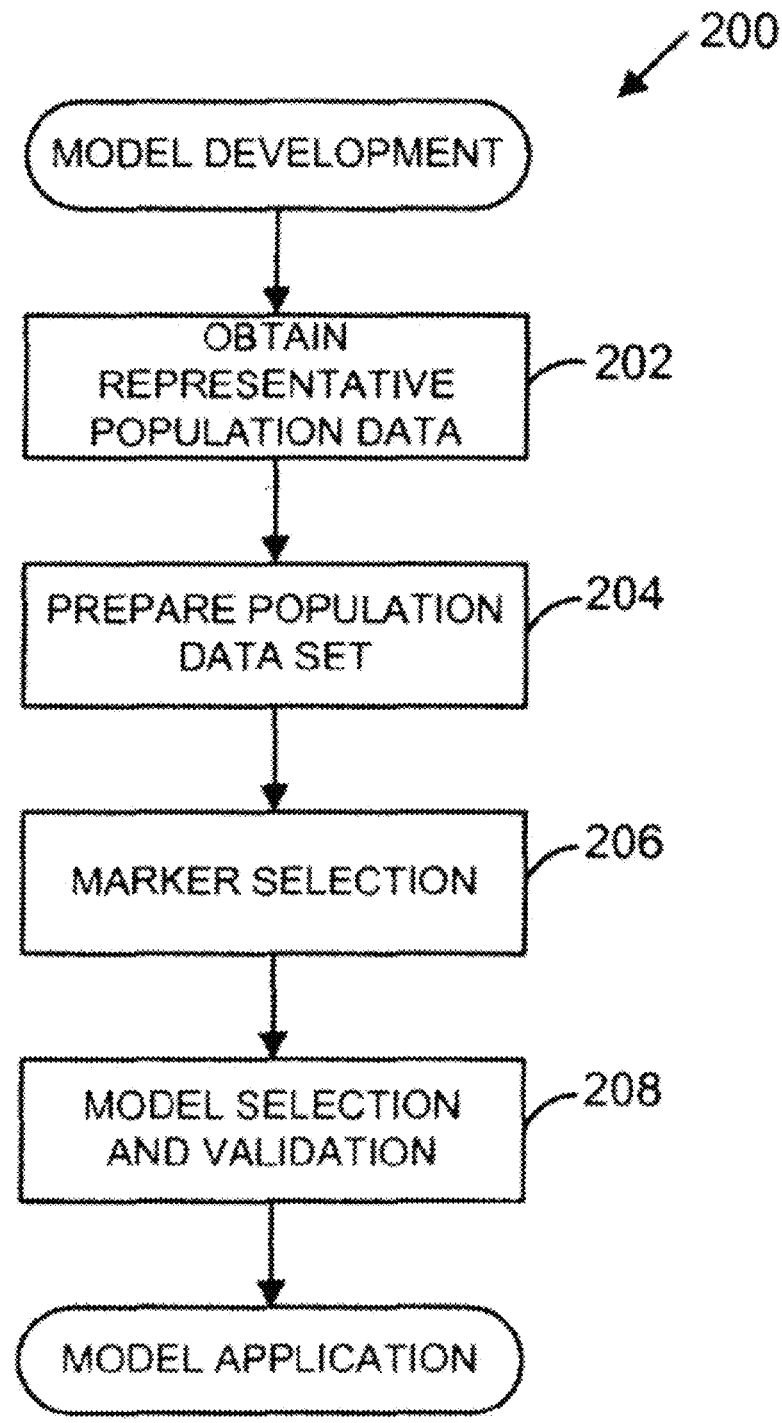
FIG. 12 is a flow diagram, which describes an example of a method for developing a model that can be used to determine the inflammatory disease activity of a person or population.

Use of the Present Teachings in the Diagnosis, Prognosis, or Assessment of Disease Model Development Process An exemplary method for developing predictive models to determine the inflammatory disease activity of a subject or population is shown by the flow diagram of FIG. 12 (200). Biomarker data from a representative population, as described herein, is obtained (202). This biomarker data can be derived through a variety of methods, including prospective, retrospective, cross-sectional, or longitudinal studies that involve interventions or observations of the representative subjects or populations from one or more time points. The biomarker data can be obtained from a single study or multiple studies. Subject and population data can generally include data pertaining to the subjects' disease status and/or clinical assessments, which can be used for training and validating the algorithms for use in the present teachings, wherein the values of the biomarkers described herein are correlated to the desired clinical measurements.

Data within the representative population dataset is then prepared (204) so as to fit the requirements of the model that will be used for biomarker selection, described below. A variety of methods of data preparation can be used, such as transformations, normalizations, and gap-fill techniques including nearest neighbor interpolation or other pattern recognition techniques. The data preparation techniques that are useful for different model types are well-known in the art.

Biomarkers are then selected for use in the training of the model to determine inflammatory disease activity (206). Various models can be used to inform this selection, and biomarker data are chosen from the dataset providing the most reproducible results. Methods to evaluate biomarker performance can include, e.g., bootstrapping and cross-validation.

After the biomarkers are selected, the model to be used to determine inflammatory disease activity can be selected. For specific examples of statistical methods useful in designing predictive models, see Calculation of the MBDA score.

For the particular selection model used with a dataset, biomarkers can be selected based on such criteria as the biomarker's ranking among all candidate markers, the biomarker's statistical significance in the model, and any improvement in model performance when the biomarker is added to the model. Tests for statistical significance can include, for example, correlation tests, t-tests, and analysis of variance (ANOVA). Models can include, for example, regression models such as regression trees and linear models, and classification models such as logistic regression, Random Forest, SVM, tree models, and LDA. Examples of these are described herein.

In those cases where individual biomarkers are not alone indicative of inflammatory disease activity, biomarker combinations can be applied to the selection model. Instead of univariate biomarker selection, for example, multivariate biomarker selection can be used. One example of an algorithm useful in multivariate biomarker selection is a recursive feature selection algorithm. Biomarkers that are not alone good indicators of inflammatory disease activity may still be useful as indicators when in combination with other biomarkers, in a multivariate input to the model, because each biomarker may bring additional information to the combination that would not be informative where taken alone.

Next, selection, training and validation are performed on the model for assessing disease activity (208). Models can be selected based on various performance and/or accuracy criteria, such as described herein. By applying datasets to different models, the results can be used to select the best models, while at the same time the models can be used to determine which biomarkers are statistically significant for inflammatory disease activity. Combinations of models and biomarkers can be compared and validated in different datasets. The comparisons and validations can be repeated in order to train and/or choose a particular model.

Figure 13:
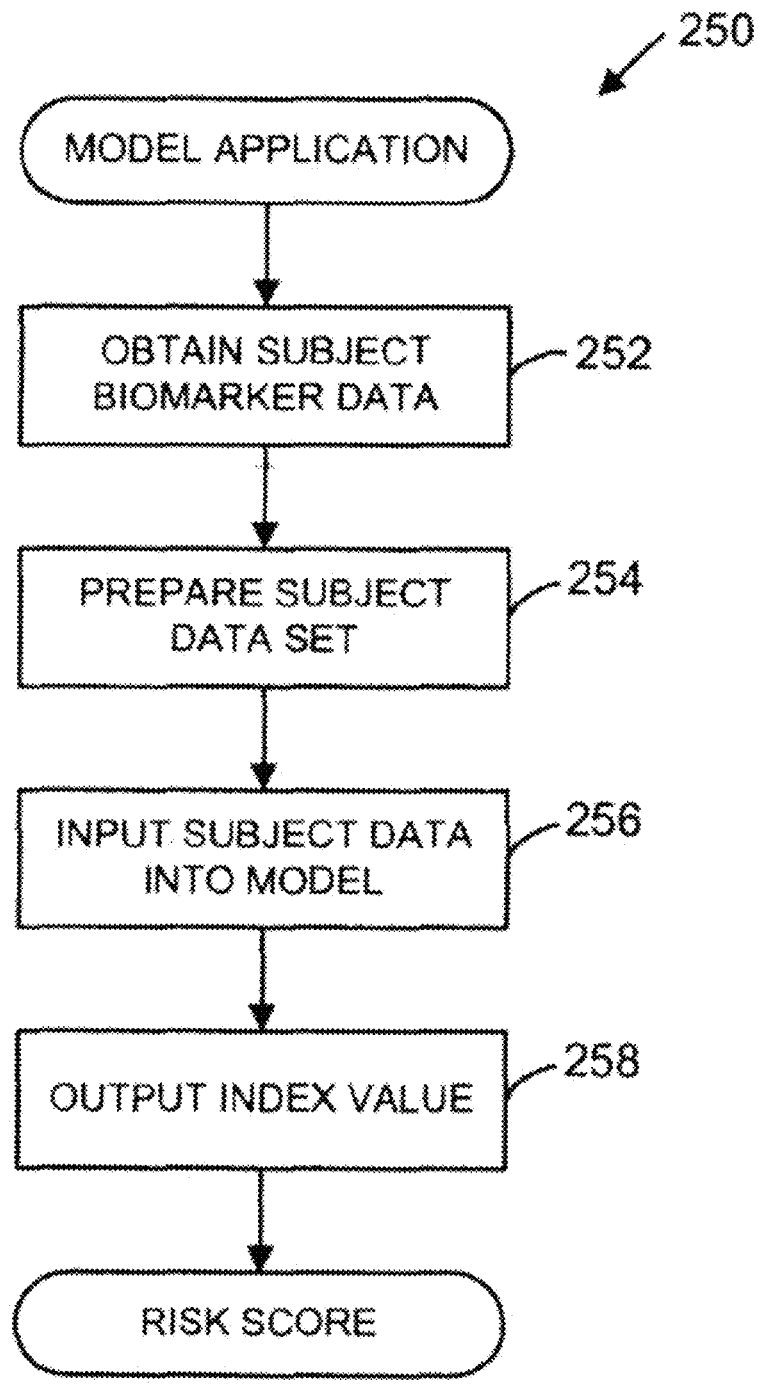
FIG. 13 is a flow diagram, which describes an example of a method for using the model of FIG. 12 to determine the inflammatory disease activity of a subject or population.

FIG. 13 is a flow diagram of an exemplary method (250) of using a model as developed above to determine the inflammatory disease activity of a subject or a population. Biomarker data is obtained from the subject at (252). This data can be obtained by a variety of means, including but not limited to physical examinations, self-reports by the subject, laboratory testing, medical records and charts. Subject data can then be prepared (254) via transformations, logs, normalizations, and so forth, based on the particular model selected and trained in FIG. 12. The data is then input into the model for evaluation (256), which outputs an index value (258); e.g., an MBDA score. Examples as to how a model can be used to evaluate a subject's biomarkers and output a MBDA value are provided herein.

In some embodiments of the present teachings, the disclosed biomarkers group can be used in the derivation of a MBDA score, as described herein, which MBDA score can be used to provide diagnosis, prognosis and monitoring of disease state and/or disease activity in inflammatory disease and in autoimmune disease such as axSpA. In certain embodiments, the MBDA score can be used to provide diagnosis, prognosis and monitoring of disease state and/or disease activity of axSpA.

Identifying the state of inflammatory disease in a subject allows for a prognosis of the disease, and thus for the informed selection of, initiation of, adjustment of or increasing or decreasing various therapeutic regimens in order to delay, reduce or prevent that subject's progression to a more advanced disease state. In some embodiments, therefore, subjects can be identified as having a particular level of inflammatory disease activity and/or as being at a particular state of disease, based at least in part on the determination of their MBDA scores, and so can be selected to begin or accelerate treatment, as treatment is defined herein, to prevent or delay the further progression of inflammatory disease. In other embodiments, subjects that are identified via their MBDA scores as having a particular level of inflammatory disease activity, and/or as being at a particular state of inflammatory disease, can be selected to have their treatment decreased or discontinued, where improvement or remission in the subject is seen.

Blood-based biomarkers that can be used according to the present teachings to detect the current rate of spine and sacroiliac joint destructive processes can also be applied in a powerful prognostic approach to identifying subjects at highest risk of accelerated bone and cartilage damage. In some embodiments of the present teachings, the disclosed biomarkers can be measured from subjects' or a subject's samples obtained at various time points (e.g., longitudinally), to obtain a series of MBDA scores, and the scores can then be combined with radiological results at various time points and so be used to provide a measurement of disease progression. The association of the MBDA scores can be analyzed statistically for correlation (e.g., Spearman correlation) using multivariate analysis to create single time point or longitudinal hierarchical linear models and ensure accuracy. Serum biomarkers can thus be used as an alternative to ultrasound, MRI, CT, and radiological results in estimating the risk and rates of progression of disease, and predicting spine and sacroiliac joint damage in axSpA. Predictive models using biomarkers can thus be used in diagnostic methods according to the present teachings to identify subjects who need more aggressive treatment, and earlier, and can thereby improve subject outcomes. In other embodiments, the MBDA scores from one subject can be compared with each other, for observations of longitudinal trending as an effect of, e.g., choice or effectiveness of therapeutic regimen, or as a result of the subject's response to treatment regimens, or a comparison of the subject's responses to different regimens.

The present teachings indicate that the disclosed biomarkers are a strong predictor of disease activity over time; e.g., longitudinally. This is a significant finding from a clinical care perspective. Currently no tests are available to accurately measure and track axSpA disease activity over time in the clinic. The tests developed from various embodiments of the present teachings will facilitate the monitoring of disease activity and Tight Control practices, and result in improved control of disease activity and improved clinical outcomes.

Regarding the need for early and accurate diagnosis of axSpA, recent advances in axSpA treatment provide a means for more profound disease management and optimal treatment of axSpA within the first months of symptom onset, which in turn result in significantly improved outcomes. Unfortunately, most subjects do not receive optimal treatment within this narrow window of opportunity, resulting in poorer outcomes and irreversible spinal and sacroiliac joint damage, in part because of the limits of current diagnostic laboratory tests. Numerous difficulties exist in diagnosing axSpA in a subject. This is in part because at their early stages, symptoms may not be fully differentiated. In various embodiments of the present teachings, multi-biomarker algorithms useful in diagnostic methods for detecting axSpA can be derived from the disclosed biomarkers. This aspect of the present teachings has the potential to improve both the accuracy of axSpA diagnosis, and the speed of axSpA detection.

Classifying Disease Activity

In some embodiments of the present teachings, the MBDA score, derived as described herein, can be used to classify or assess inflammatory disease activity; e.g., as high, medium, low, or remission. In some embodiments of the present teachings, autoimmune disease activity can be so classified or assessed. In other embodiments, axSpA disease activity can be so classified or scored. Using AS disease as an example, because the MBDA score correlates well and with high accuracy with clinical assessments of AS (e.g., with a ASDAS score), MBDA cut-off scores can be set at predetermined levels to indicate levels of AS disease activity, and to correlate with the cut-offs traditionally established for rating AS activity via ASDAS scores. Because the MBDA score correlates well with traditional clinical assessments of inflammatory disease activity, e.g. in AS, in other embodiments of the present teachings bone damage itself in a subject or population, and thus disease progression, can be tracked via the use and application of the MBDA score. In other words, the present teachings disclose methods of detecting or measuring damage (and/or disease progression) by determining a patient sample's MBDA score as a surrogate for (e.g., in place of) traditional clinical assessments.

One example of a disease activity score is the ASDAS score, which was developed by the Assessment of SpondyloArthritis International Society. The score includes the combination of five criteria: patient-reported assessments of back pain, duration of morning stiffness, peripheral joint pain and/or swelling, general well-being, and a serologic marker of inflammation (erythrocyte sedimentation rate (ESR) or C-reactive protein (CRP)). See e.g., Zochling, *Arthritis Care & Research* 63:S47-S58 (2011)). The modified Stoke Ankylosing Spondylitis Spinal Score (mSASSS) is a known radiographic scoring system that is the sum of lateral views of the lumbar and cervical spine scores. See, e.g., Creemers et al. *Ann. Rheum Dis.* 64:127-129 (2005).

Disease activity can further be used to predict risk for progressive damage to a subject's spine and/or sacroiliac joints. As described herein, axSpA can be categorized as either nr-axSpA or AS. Disease activity scores that correlate with AS are indicative of higher risks of progressive damage to the spine and sacroiliac joints. Conversely, disease activity scores that correlate with nr-axSpA are indicative of lower risks of progressive damage to the spine and sacroiliac joints.

These properties of the disclosed biomarkers can be used for several purposes. On a subject-specific basis, they provide a context for understanding the relative level of disease activity. The rating of disease activity can be used, e.g., to guide the clinician in determining treatment, in setting a treatment course, and/or to inform the clinician that the subject is in remission. Moreover, it provides a means to more accurately assess and document the qualitative level of disease activity in a subject. It is also useful from the perspective of assessing clinical differences among populations of subjects within a practice. For example, this tool can be used to assess the relative efficacy of different treatment modalities. Moreover, it is also useful from the perspective of assessing clinical differences among different practices. This would allow physicians to determine what global level of disease control is achieved by their colleagues, and/or for healthcare management groups to compare their results among different practices for both cost and comparative effectiveness.

In some embodiments of the present teachings, the MBDA score, derived as described herein, can be used to rate axSpA disease activity; e.g., as high, medium or low. The score can be varied based on a set of values chosen by the practitioner. For example, a score can be set such that a value is given a range from 0-100, and a difference between two scores would be a value of at least one point. The practitioner can then assign disease activity based on the values. For example, in some embodiments a score of 1 to 29 represents a low level of disease activity, a score of 30 to 44 represents a moderate level of disease activity, and a score of 45 to 100 represents a high level of disease activity. The disease activity score can change based on the range of the score. For example a score of 1 to 58 can represent a low level of disease activity when a range of 0-200 is utilized. Differences can be determined based on the range of score possibilities. For example, if using a score range of 0-100, a small difference in scores can be a difference of about 1, 2, 3, 4, 5, 6, 7, 8, 9, or 10 points; a moderate difference in scores can be a difference of about 4, 5, 6, 7, 8, 9, 10, 11, 12, 13, 14, 15, 16, 17, 18, 19, 20, 21, 22, 23, 24, 25, 26, 27, 28, 29, or 30 points; and large differences can be a change in about 14, 15, 16, 17, 18, 19, 20, 21, 22, 23, 24, 25, 26, 27, 28, 29, 30, 35, 40, 45, or 50 points. Thus, by way of example, a practitioner can define a small difference in scores as about ≤6 points, a moderate difference in scores as about 7-20 points, and a large difference in scores as about >20 points. The difference can be expressed by any unit, for example, percentage points. For example, a practitioner can define a small difference as about ≤6 percentage points, moderate difference as about 7-20 percentage points, and a large difference as about >20 percentage points.

The MBDA score can be used for several purposes. On a subject-specific basis, it provides a context for understanding the relative level of disease activity. The MBDA rating of disease activity can be used, e.g., to guide the clinician in determining treatment, in setting a treatment course, and/or to inform the clinician that the subject is in remission. Moreover, it provides a means to more accurately assess and document the qualitative level of disease activity in a subject. It is also useful from the perspective of assessing clinical differences among populations of subjects within a practice. For example, this tool can be used to assess the relative efficacy of different treatment modalities. Moreover, it is also useful from the perspective of assessing clinical differences among different practices. This would allow physicians to determine what global level of disease control is achieved by their colleagues, and/or for healthcare management groups to compare their results among different practices for both cost and comparative effectiveness. Because the MBDA score demonstrates strong association with established disease activity assessments, the MBDA score can provide a quantitative measure for monitoring the extent of subject disease activity, and response to treatment.

Subject Screening

Certain embodiments of the present teachings can also be used to screen subject populations in any number of settings. For example, a health maintenance organization, public health entity or school health program can screen a group of subjects to identify those requiring interventions, as described above. Other embodiments of these teachings can be used to collect disease activity data on one or more populations of subjects, to identify subject disease status in the aggregate, in order to, e.g., determine the effectiveness of the clinical management of a population, or determine gaps in clinical management. Insurance companies (e.g., health, life, or disability) may request the screening of applicants in the process of determining coverage for possible intervention. Data collected in such population screens, particularly when tied to any clinical progression to conditions such as inflammatory disease and axSpA, will be of value in the operations of, for example, health maintenance organizations, public health programs and insurance companies.

Such data arrays or collections can be stored in machine-readable media and used in any number of health-related data management systems to provide improved healthcare services, cost-effective healthcare, and improved insurance operation, among other things. See, e.g., U.S. Patent Application No. 2002/0038227; U.S. Patent Application No. 2004/0122296; U.S. Patent Application No. 2004/0122297; and U.S. Pat. No. 5,018,067. Such systems can access the data directly from internal data storage or remotely from one or more data storage sites as further detailed herein. Thus, in a health-related data management system, wherein it is important to manage inflammatory disease progression for a population in order to reduce disease-related employment productivity loss, disability and surgery, and thus reduce healthcare costs in the aggregate, various embodiments of the present teachings provide an improvement comprising the use of a data array encompassing the biomarker measurements as defined herein, and/or the resulting evaluation of disease status and activity from those biomarker measurements.

Measuring Accuracy and Performance of the Present Teachings

The performance of the present teachings can be assessed in any of various ways. Assessing the performance of an embodiment of the present teachings can provide a measurement of the accuracy of that embodiment, where, e.g., that embodiment is a predictive model, or a test, assay, method or procedure, whether diagnostic or prognostic. This accuracy assessment can relate to the ability of the predictive model or the test to determine the inflammatory disease activity status of a subject or population. In other embodiments, the performance assessment relates to the accuracy of the predictive model or test in distinguishing between subjects with or without inflammatory disease. In other embodiments, the assessment relates to the accuracy of the predictive model or test in distinguishing between states of inflammatory disease in one subject at different time points.

The distinguishing ability of the predictive model or test can be based on whether the subject or subjects have a significant alteration in the levels of one or more biomarkers. In some embodiments a significant alteration, in the context of the present teachings, can mean that the measurement of the biomarkers, as represented by the MBDA score computed by the MBDA formula as generated by the predictive model, is different than some predetermined MBDA cut-off point (or threshold value) for those biomarkers when input to the MBDA formula as described herein. This significant alteration in biomarker levels as reflected in differing MBDA scores can therefore indicate that the subject has inflammatory disease, or is at a particular state or severity of inflammatory disease. The difference in the levels of biomarkers between the subject and normal, in those embodiments where such comparisons are done, is preferably statistically significant, and can be an increase in biomarker level or levels, or a decrease in biomarker level or levels. In some embodiments of the present teachings, a significant alteration can mean that a MBDA score is derived from measuring the levels of one or more biomarkers, and this score alone, without comparison to some predetermined cut-off point (or threshold value) for those biomarkers, indicates that the subject has inflammatory disease or has a particular state of inflammatory disease. Further, achieving increased analytical and clinical accuracy may require that combinations of three or more biomarkers be used together in panels, and combined with mathematical algorithms derived from predictive models to obtain the MBDA score.

Use of statistical values such as the area under the curve (AUC), and specifically the AUC as it relates to the receiver/operator curve (ROC), encompassing all potential threshold or cut-off point values is generally used to quantify predictive model performance. Acceptable degrees of accuracy can be defined. In certain embodiments of the present teachings, an acceptable degree of accuracy can be one in which the AUC for the ROC is 0.60 or higher.

In general, defining the degree of accuracy for the relevant predictive model or test (e.g., cut-off points on a ROC), defining an acceptable AUC value, and determining the acceptable ranges in relative concentration of what constitutes an effective amount of the biomarkers of the present teachings, allows one of skill in the art to use the biomarkers of the present teachings to identify inflammatory disease activity in subjects or populations with a pre-determined level of predictability and performance.

In various embodiments of the present teachings, measurements from multiple biomarkers can be combined into a single value, the MBDA score, using various statistical analyses and modeling techniques as described herein. Because the MBDA score demonstrates strong association with established disease activity assessments, such as ASDAS, the MBDA score can provide a quantitative measure for monitoring the extent of subject disease activity, and response to treatment.

Calculation of the MBDA Score

In some embodiments of the present teachings, inflammatory disease activity in a subject is measured by: determining the levels in inflammatory disease subject serum of three or more biomarkers, then applying an interpretation function to transform the biomarker levels into a single MBDA score, which provides a quantitative measure of inflammatory disease activity in the subject. As discussed above and demonstrated in the Examples below, a MBDA score derived in this way according to the present teachings correlates well with traditional clinical and diagnostic assessments of inflammatory disease activity (e.g., a ASDAS score in AS) and thus can be used as a diagnostic score to measure disease activity. In some embodiments, the disease activity so measured relates to an autoimmune disease. In some embodiments, the disease activity so measured relates to axSpA or AS.

In some embodiments, the interpretation function is based on a predictive model. Established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Logistic Regression is the traditional predictive modeling method of choice for dichotomous response variables; e.g., treatment 1 versus treatment 2. It can be used to model both linear and non-linear aspects of the data variables and provides readily interpretable odds ratios.

Discriminant Function Analysis (DFA) uses a set of analytes as variables (roots) to discriminate between two or more naturally occurring groups. DFA is used to test analytes that are significantly different between groups. A forward step-wise DFA can be used to select a set of analytes that maximally discriminate among the groups studied. Specifically, at each step all variables can be reviewed to determine which will maximally discriminate among groups. This information is then included in a discriminative function, denoted a root, which is an equation consisting of linear combinations of analyte concentrations for the prediction of group membership. The discriminatory potential of the final equation can be observed as a line plot of the root values obtained for each group. This approach identifies groups of analytes whose changes in concentration levels can be used to delineate profiles, diagnose and assess therapeutic efficacy. The DFA model can also create an arbitrary score by which new subjects can be classified as either "healthy" or "diseased." To facilitate the use of this score for the medical community the score can be rescaled so a value of 0 indicates a healthy individual and scores greater than 0 indicate increasing disease activity.

Classification and regression trees (CART) perform logical splits (if/then) of data to create a decision tree. All observations that fall in a given node are classified according to the most common outcome in that node. CART results are readily interpretable—one follows a series of if/then tree branches until a classification results.

Support vector machines (SVM) classify objects into two or more classes. Examples of classes include sets of treatment alternatives, sets of diagnostic alternatives, or sets of prognostic alternatives. Each object is assigned to a class based on its similarity to (or distance from) objects in the training data set in which the correct class assignment of each object is known. The measure of similarity of a new object to the known objects is determined using support vectors, which define a region in a potentially high dimensional space (>R6).

The process of bootstrap aggregating, or "bagging," is computationally simple. In the first step, a given dataset is randomly resampled a specified number of times (e.g., thousands), effectively providing that number of new datasets, which are referred to as "bootstrapped resamples" of data, each of which can then be used to build a model. Then, in the example of classification models, the class of every new observation is predicted by the number of classification models created in the first step. The final class decision is based upon a "majority vote" of the classification models; i.e., a final classification call is determined by counting the number of times a new observation is classified into a given group, and taking the majority classification (33%+ for a three-class system). In the example of logistical regression models, if a logistical regression is bagged 1000 times, there will be 1000 logistical models, and each will provide the probability of a sample belonging to class 1 or 2.

Curds and Whey (CW) using ordinary least squares (OLS) is another predictive modeling method. See L. Breiman and J H Friedman, *J. Royal. Stat. Soc. B* 1997, 59(1):3-54. This method takes advantage of the correlations between response variables to improve predictive accuracy, compared with the usual procedure of performing an individual regression of each response variable on the common set of predictor variables X. In CW, Y=XB*S, where Y=($y_{kj}$) with k for the $k^{th}$ patient and j for $j^{th}$ response (j=1 for TJC, j=2 for SJC, etc.), B is obtained using OLS, and S is the shrinkage matrix computed from the canonical coordinate system. Another method is Curds and Whey and Lasso in combination (CW-Lasso). Instead of using OLS to obtain B, as in CW, here Lasso is used, and parameters are adjusted accordingly for the Lasso approach.

Many of these techniques are useful either combined with a biomarker selection technique (such as, for example, forward selection, backwards selection, or stepwise selection), or for complete enumeration of all potential panels of a given size, or genetic algorithms, or they can themselves include biomarker selection methodologies in their own techniques. These techniques can be coupled with information criteria, such as Akaike's Information Criterion (AIC), Bayes Information Criterion (BIC), or cross-validation, to quantify the tradeoff between the inclusion of additional biomarkers and model improvement, and to minimize overfit. The resulting predictive models can be validated in other studies, or cross-validated in the study they were originally trained in, using such techniques as, for example, Leave-One-Out (LOO) and 10-Fold cross-validation (10-Fold CV).

In some embodiments of the present teachings, it is not required that the MBDA score be compared to any predetermined "reference," "normal," "control," "standard," "healthy," "pre-disease" or other like index, in order for the MBDA score to provide a quantitative measure of inflammatory disease activity in the subject.

In other embodiments of the present teachings, the amount of the biomarker(s) can be measured in a sample and used to derive a MBDA score, which MBDA score is then compared to a "normal" or "control" level or value, utilizing techniques such as, e.g., reference or discrimination limits or risk defining thresholds, in order to define cut-off points and/or abnormal values for inflammatory disease. The normal level then is the level of one or more biomarkers or combined biomarker indices (e.g., MBDA score) typically found in a subject who is not suffering from the inflammatory disease under evaluation or in whom disease activity is known to be some particular (e.g., clinically acceptable) level. Other terms for "normal" or "control" are, e.g., "reference," "index," "baseline," "standard," "healthy," "pre-disease," etc. Such normal levels can vary, based on whether a biomarker is used alone or in a formula combined with other biomarkers to output a score. Alternatively, the normal level can be a database of biomarker patterns from previously tested subjects who did not convert to the inflammatory disease under evaluation over a clinically relevant time period. Reference (normal, control) values can also be derived from, e.g., a control subject or population whose inflammatory disease activity level or state is known. In some embodiments of the present teachings, the reference value can be derived from one or more subjects who have been exposed to treatment for inflammatory disease, or from one or more subjects who are at low risk of developing inflammatory disease, or from subjects who have shown improvements in inflammatory disease activity factors (such as, e.g., clinical parameters as defined herein) as a result of exposure to treatment. In some embodiments the reference value can be derived from one or more subjects who have not been exposed to treatment; for example, samples can be collected from (a) subjects who have received initial treatment for inflammatory disease, and (b) subjects who have received subsequent treatment for inflammatory disease, to monitor the progress of the treatment. A reference value can also be derived from disease activity algorithms or computed indices from population studies.

Systems for Implementing Disease Activity Tests

Tests for measuring disease activity according to various embodiments of the present teachings can be implemented on a variety of systems typically used for obtaining test results, such as results from immunological or nucleic acid detection assays. Such systems may comprise modules that automate sample preparation, that automate testing (e.g., measuring biomarker levels), that facilitate testing of multiple samples, and/or are programmed to assay the same test or different tests on each sample. In some embodiments, the testing system comprises one or more of a sample preparation module, a clinical chemistry module, and an immunoassay module on one platform. Testing systems can be designed such that they also comprise modules to collect, store, and track results, such as by connecting to and utilizing a database residing on hardware. Examples of these modules include physical and electronic data storage devices as are known in the art, such as a hard drive, flash memory, and magnetic tape. Test systems also generally comprise a module for reporting and/or visualizing results. Some examples of reporting modules include a visible display or graphical user interface, links to a database, a printer, etc. See section Machine-readable storage medium, below.

One embodiment of the present invention comprises a system for determining the inflammatory disease activity of a subject. In some embodiments, the system employs a module for applying a formula to an input comprising the measured levels of biomarkers in a panel, as described herein, and outputting a disease activity index score. In some embodiments, the measured biomarker levels are test results, which serve as inputs to a computer that is programmed to apply the formula. The system may comprise other inputs in addition to or in combination with biomarker results in order to derive an output disease activity index; e.g., one or more clinical parameters such as therapeutic regimen, TJC, SJC, morning stiffness, damage to the spine and/or sacroiliac joints, radiographic changes and other imaging, gender/sex, age, race/ethnicity, disease duration, height, weight, body-mass index, family history, CCP status, RF status, ESR, smoker/non-smoker, etc. In some embodiments the system can apply the formula to biomarker level inputs, and then output a disease activity score that can then be analyzed in conjunction with other inputs such as other clinical parameters. In other embodiments, the system is designed to apply the formula to the biomarker and non-biomarker inputs (such as clinical parameters) together, and then report a composite output disease activity index.

A number of testing systems are presently available that can be used to implement various embodiments of the present teachings. See, for example, the ARCHITECT series of integrated immunochemistry systems—high-throughput, automated, clinical chemistry analyzers (ARCHITECT is a registered trademark of Abbott Laboratories, Abbott Park, Ill. 60064). See C. Wilson et al., "Clinical Chemistry Analyzer Sub-System Level Performance," American Association for Clinical Chemistry Annual Meeting, Chicago, Ill., Jul. 23-27, 2006; and, H J Kisner, "Product development: the making of the Abbott ARCHITECT," *Clin. Lab. Manage. Rev.* 1997 November-December, 11(6):419-21; A. Ognibene et al., "A new modular chemiluminescence immunoassay analyser evaluated," *Clin. Chem. Lab. Med.* 2000 March, 38(3):251-60; J W Park et al., "Three-year experience in using total laboratory automation system," Southeast Asian J. Trop. Med. Public Health 2002, 33 Suppl 2:68-73; D. Pauli et al., "The Abbott Architect c8000: analytical performance and productivity characteristics of a new analyzer applied to general chemistry testing," *Clin. Lab.* 2005, 51(1-2):31-41.

Another testing system useful for embodiments of the present teachings is the VITROS system (VITROS is a registered trademark of Johnson & Johnson Corp., New Brunswick, N.J.)—an apparatus for chemistry analysis that is used to generate test results from blood and other body fluids for laboratories and clinics. Another testing system is the DIMENSION system (DIMENSION is a registered trademark of Dade Behring Inc., Deerfield Ill.)—a system for the analysis of body fluids, comprising computer software and hardware for operating the analyzers, and analyzing the data generated by the analyzers.

The testing required for various embodiments of the present teachings, e.g. measuring biomarker levels, can be performed by laboratories such as those certified under the Clinical Laboratory Improvement Amendments (42 U.S.C. Section 263(a)), or by laboratories certified under any other federal or state law, or the law of any other country, state or province that governs the operation of laboratories that analyze samples for clinical purposes.

Biomarker Selection

The biomarkers and methods of the present teachings allow one of skill in the art to monitor or assess a subject's inflammatory and/or autoimmune disease activity, such as for AxSpA, with a high degree of accuracy. For the initial comparison of observed biomarker with AxSpA disease activity, the disease activity for each subject was based upon clinical parameters, such as the ASDAS score.

Analyte biomarkers can be selected for use in the present teachings to form a panel or group of markers. Table 1 lists the 17 biomarkers from the DA-17 panel of biomarkers, and calprotectin, that are associated with AS. The present teachings describe the set of biomarkers as one set or panel of markers that is strongly associated with inflammatory disease, and especially axSpA and AS, when used in particular combinations to derive a MBDA score, based on their correlation with traditional clinical assessments of disease; in the example of AS, by their correlation with ASDAS. See Example 1. As an example, one embodiment of the present teachings comprises a method of determining AS disease activity in a subject comprising measuring the levels of at least 2, 3, 4, 5, 6, 7, 8, 9, 10, 11, 12, 13, 14, 15, 16, 17, or 18 biomarkers from Table 1, wherein the at least three biomarkers are selected from the group consisting of calprotectin (dimer of S100A8 and S100A9 protein subunits; MRP-8/14); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); interleukin 6 (IL6); interleukin 8 (IL8); interleukin 1, beta (IL1B); interleukin 6 receptor (IL6R); leptin (LEP); Macrophage-derived chemokine (MDC); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA); then, using these observed biomarker levels to derive a disease activity index score for the subject via an interpretation function, which score provides a quantitative measure of AS disease activity in that subject.

TABLE 1

| Symbol | Full name | NCBI RefSeq |
|---|---|---|
| VCAM-1 | Vascular cell adhesion molecule-1 | NP_001069.1 |
| EGF | Epidermal growth factor | NP_001954.2 |
| VEGF-A | Vascular endothelial growth factor A | NP_001020539.2 |
| IL-6 | Interleukin-6 | NP_000591.1 |
| TNF-R1 | Tumor necrosis factor receptor, type 1 | NP_001056.1 |
| MMP-1 | Matrix metalloproteinase-1 | NP_002412.1 |
| MMP-3 | Matrix metalloproteinase-3 | NP_002413.1 |
| YKL-40 | Chitinase 3-like 1 | NP_001267.2 |
| Leptin | Leptin | NP_000221.1 |
| Resistin | Resistin | NP_065148.1 |
| SAA | Serum amyloid | NP_000322.2 |
| CRP | C-reactive protein | NP_000558.2 |
| MDC | Macrophage-derived chemokine | NP_002981.2 |
| IL-6R | Interleukin 6 receptor | NP_000565.1 |
| ICAM-1 | Intercellular adhesion molecule 1 | NP_001069.1 |
| IL-8 | Interleukin-8 | NP_000575.1 |
| IL-1B | Interleukin-1 beta | NP_000567.1 |
| S100A8 | Calprotectin | NP_002955.2 |
| S100A9 | Calprotectin | NP_002956.1 |

One skilled in the art will recognize that the biomarkers presented herein encompass all forms and variants of these biomarkers, including but not limited to polymorphisms, isoforms, mutants, derivatives, transcript variants, precursors (including nucleic acids and pre- or pro-proteins), cleavage products, receptors (including soluble and transmembrane receptors), ligands, protein-ligand complexes, protein-protein homo- or heteropolymers, post-translationally modified variants (such as, e.g., via cross-linking or glycosylation), fragments, and degradation products, as well as any multi-unit nucleic acid, protein, and glycoprotein structures comprising any of the biomarkers as constituent subunits of the fully assembled structure.

As described in Example 1, the candidate biomarkers can include any biomarker present in the DA-17 panel of biomarkers. All biomarker assays can be performed at controlled ambient temperature of 20±5° C. Multispot 96-well plates (MSD) can be spotted in specific locations with biomarker-specific capture antibodies for. Biomarker concentrations can be determined using 3 separate multiplex panels, based on sample dilution requirements. Pre-diluted standards and QC run controls can be loaded onto the plate alongside diluted patient samples and diluted process controls. Diluted serum samples and process controls can be prepared using a validated Hamilton STAR (Reno, Nev., USA) automated dilution platform.

The VECTRA® DA biomarkers can be assayed to determine measurability. To establish the assay's dynamic range for each biomarker, the limit of quantitation (LOQ), defined as the actual amount of analyte that can be reliably detected in a sample and at which the total analytical error meets the requirements for accuracy and precision, can be determined as described in EP17-A Clinical Laboratory Standards Institute (CLSI). Acceptable accuracy at the LOQ can be defined as 80-120% recovery of the input mass based on the vendor's specification for each particular protein, and the acceptable precision requirement at the LOQ can be defined as a 20% CV. An assay's analytical measurable range can be defined as the difference between the upper limit (ULOQ) and the lower limit (LLOQ). The clinically reportable or dynamic range for an assay can be defined as the dilution-adjusted range. Non-VECTRA® DA biomarkers can be analyzed via commercially available standard ELISAs.

Univariate Analysis

For intra-run precision of an MBDA (multi-biomarker disease activity) score, 4 serum pools can be each run 14 times on a single plate. Two plates from each of 2 different lots can be evaluated, and the means and % CVs for the MBDA score can be calculated. Associations can be calculated between the MBDA scores and ASDAS-ESR, ASDAS-CRP, and mSASSS (see FIGS. 1, 3, and 4). Associations can be further calculated between the MBDA scores and the patient global, back pain, nocturnal pain, and BASFI assessments (see FIG. 2).

The most informative biomarkers for overall assessment of axSpA or AS disease activity can then be chosen. An importance score can be generated for each biomarker through an array of univariate and multivariate analyses. Univariate analysis can performed to evaluate the correlation between each individual biomarker and each clinical measure.

Assessment Scoring

Samples acquired from the cohorts can be analyzed using selected biomarkers. The Ankylosing Spondylitis Disease Activity Score (ASDAS) and mSASSS scores can be calculated for each sample.

Strong correlations can be observed between the 12 biomarker VECTRA® DA MBDA panel and the ASDAS (ESR and CRP) scores (see FIG. 1). Strong correlations can be further observed between the 12 biomarker VECTRA® DA MBDA panel and other clinical assessment standards such as mSASSS and BASDAI (see FIG. 1); and patient global, back pain, nocturnal pain, and BASFI (see FIG. 2). See FIGS. 3-7 for an illustration on the correlations of exemplary individual biomarker to ASDAS-ESR, ASDAS-CRP, and mSASSS.

The present teachings describe a robust, stepwise development process for identifying a panel or panels of biomarkers that are strongly predictive of autoimmune disease, such as axSpA, activity. Multivariate algorithmic combinations of specific biomarkers as described herein exceed the prognostic and predictive power of individual biomarkers known in the art, because the combinations comprise biomarkers that represent a broad range of disease mechanisms, which no individual biomarker does. As a consequence of the diversity of pathways represented by the combinations as taught herein, the methods of the present teachings are useful in the clinical assessment of individual subjects, despite the heterogeneity of the pathology of the disease assessed.

The group of biomarkers described herein was identified through a selection process comprising rigorous correlation studies of an initial large, comprehensive set of candidate protein biomarkers. The methodology employed in selecting the biomarkers resulted in a set of markers especially useful in quantifying axSpA disease activity, by providing the clinician with a unique and broad look at axSpA disease biology. The biomarkers of the present teachings are thus more effective in quantifying disease activity than single biomarkers or randomly selected groupings of biomarkers.

Additionally, because the serum levels of certain protein biomarkers are known to fluctuate in an individual, depending on disease activity, in some embodiments of the present teachings the clinician could select those biomarkers for generating a MBDA score, and thus obtain a more concise overview of the subject's present disease activity status.

Moreover, the process of comprehensive candidate biomarker identification and subsequent staged correlation-based analyses in a series of independent cohorts, as described in the Examples that follow, results in the identification of a panel or panels of biomarkers that have significant correlation to disease activity.

Modifications for Response to Treatment

In certain embodiments of the present teachings, the disclosed biomarkers can be used to determine a subject's response to treatment for inflammatory disease such as axSpA. Measuring levels of an effective amount of biomarkers also allows for subject-specific biological information, which will be informative for therapy decision and will facilitate therapy response monitoring, and should result in more rapid and more optimized treatment, better control of disease activity, and an increase in the proportion of subjects achieving remission.

Various embodiments of the present teachings can be used to provide a guide to the selection of a therapeutic regimen for a subject; meaning, e.g., that treatment may need to be more or less aggressive, or a subject may need a different therapeutic regimen, or the subject's current therapeutic regimen may need to be changed or stopped, or a new therapeutic regimen may need to be adopted, etc. If desired, biological samples are obtained from the subject at various time points before, during, or after treatment.

In many embodiments, the levels of one or more analyte biomarkers or the levels of a specific panel of analyte biomarkers in a sample are compared to a reference standard ("reference standard" or "reference level") in order to direct treatment decisions. The reference standard used for any embodiment disclosed herein may comprise average, mean, or median levels of the one or more analyte biomarkers or the levels of the specific panel of analyte biomarkers in a control population. The reference standard may additionally comprise cutoff values or any other statistical attribute of the control population, such as a standard deviation from the mean levels of the one or more analyte biomarkers or the levels of the specific panel of analyte biomarkers. In some embodiments, the control population may comprise healthy individuals or individuals with axSpA.

In some embodiments, individuals with levels of one or more analyte biomarkers or levels of a specific panel of analyte biomarkers greater than the reference levels would be more likely to have axSpA. Therefore, an individual presenting with levels of the one or more analyte biomarkers or levels of the specific panel of analyte biomarkers greater than the reference standard would be a candidate for more aggressive therapy. On the other hand, an individual presenting with levels of the one or more analyte biomarkers or levels of the specific panel of analyte biomarkers less than or equal to the reference standard would be less likely to have axSpA and therefore be a candidate for less aggressive therapy.

In other embodiments, individuals with levels of one or more analyte biomarkers or levels of a specific panel of analyte biomarkers less than the reference levels would be more likely to have axSpA. Therefore, an individual presenting with levels of the one or more analyte biomarkers or levels of the specific panel of analyte biomarkers less than the reference standard would be a candidate for more aggressive therapy. On the other hand, an individual presenting with levels of the one or more analyte biomarkers or levels of the specific panel of analyte biomarkers greater than or equal to the reference standard would be less likely to have axSpA and therefore be a candidate for less aggressive therapy.

In some embodiments, a patient is treated more or less aggressively than a reference therapy. A reference therapy is any therapy that is the standard of care for axSpA. The standard of care can vary temporally and geographically, and a skilled person can easily determine the appropriate standard of care by consulting the relevant medical literature.

In some embodiments, based on a determination that levels of a panel of biomarkers is a) greater than, b) less than, c) equal to, d) greater than or equal to, or e) less than or equal to a reference standard, treatment will be either 1) more aggressive, or 2) less aggressive than a standard therapy.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Those skilled in the art can readily adapt various existing treatments, and are familiar with various aggressive and less aggressive treatments for axSpA and/or AS for use in the treatment methods described herein. "Active treatment" for axSpA and/or AS is well-understood by those skilled in the art and, as used herein, has the conventional meaning in the art. Generally speaking, active treatment for axSpA and/or AS can include anything other than "watchful waiting." Active treatment currently applied in the art of axSpA treatment can include but are not limited to administration of prophylactics or therapeutic compounds (including conventional and novel DMARDs, biologic DMARDs, non-steroidal anti-inflammatory drugs (NSAIDs) exercise regimens, physical therapy, dietary modification and/or supplementation, bariatric surgical intervention, administration of pharmaceuticals and/or anti-inflammatories (prescription or over-the-counter), and any other treatments known in the art as efficacious in preventing, delaying the onset of, or ameliorating disease. Examples of therapies that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intramuscular gold (IM gold), leflunomide (LEF), levofloxacin (LEV), and sulfasalazine (SSZ) certolizumab, JAK inhibitors, and apremilast. Examples of other conventional therapies include, but are not limited to, folinic acid, D-pencillamine, gold auranofin, gold aurothioglucose, gold thiomalate, cyclophosphamide, and chlorambucil. Examples of biologic therapies (or biologic drugs) include but are not limited to biological agents that target the tumor necrosis factor (TNF)-alpha molecules and the TNF inhibitors, such as infliximab, adalimumab, etanercept and golimumab. Other classes of biologic therapies include IL1 inhibitors such as anakinra, T-cell modulators such as abatacept, B-cell modulators such as rituximab, and IL6 inhibitors such as tocilizumab, and agents against IL12/23, IL-17, and IL-23.

In one embodiment, the practitioner adjusts the therapy based on a comparison between a reference level and the levels of one or more analyte biomarkers or the levels of a specific panel of analyte biomarkers in a sample from a patient. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In some embodiments, treatment comprises a less aggressive therapy than a reference therapy. In one embodiment a less aggressive therapy comprises not administering drugs and taking a "watchful waiting" approach. "Watchful-waiting," also sometimes called "active surveillance," also has its conventional meaning in the art. This generally means observation and regular monitoring without treatment of the underlying disease. Watching-waiting can also be suggested when the risks of aggressive therapy outweighs the possible benefits. Other treatments can be started if symptoms develop, or if there are signs that the cancer growth is accelerating.

In one embodiment a less aggressive therapy comprises delaying treatment. In one embodiment a less aggressive therapy comprises selecting and administering less potent drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy.

In one embodiment, more aggressive therapy comprises selecting and administering more potent drugs, increasing drug dosage, accelerating dose schedule, and increasing length of therapy. In some embodiments, a more aggressive therapy comprises administering a combination of drug-based and non-drug-based therapies.

Differences in the genetic makeup of subjects can result in differences in their relative abilities to metabolize various drugs, which may modulate the symptoms or state of inflammatory disease. Subjects that have inflammatory disease can vary in age, ethnicity, body mass index (BMI), total cholesterol levels, blood glucose levels, blood pressure, LDL and HDL levels, and other parameters. Accordingly, use of the biomarkers disclosed herein, both alone and together in combination with known genetic factors for drug metabolism, allow for a pre-determined level of predictability that a putative therapeutic or prophylactic to be tested in a selected subject will be suitable for treating or preventing inflammatory disease in the subject.

Combination with Clinical Parameters

Any of the aforementioned clinical parameters can also be used in the practice of the present teachings, as input to a formula or as a pre-selection criteria defining a relevant population to be measured using a particular biomarker panel and formula. As noted above, clinical parameters can also be useful in the biomarker normalization and pre-processing, or in selecting particular biomarkers, panel construction, formula type selection and derivation, and formula result post-processing.

Clinical Assessments of the Present Teachings

In some embodiments of the present teachings, panels of biomarkers and formulas are tailored to the population, endpoints or clinical assessment, and/or use that is intended. For example, the biomarker panels and formulas can be used to assess subjects for primary prevention and diagnosis, and for secondary prevention and management. For the primary assessment, the biomarker panels and formulas can be used for prediction and risk stratification for future conditions or disease sequelae, for the diagnosis of inflammatory disease, for the prognosis of disease activity and rate of change, and for indications for future diagnosis and therapeutic regimens. For secondary prevention and clinical management, the biomarker panels and formulas can be used for prognosis and risk stratification. The biomarker panels and formulas can be used for clinical decision support, such as determining whether to defer intervention or treatment, to recommend preventive check-ups for at-risk patients, to recommend increased visit frequency, to recommend increased testing, to recommend intervention, and to recommend therapy withdraw or tapering. The biomarker panels and formulas can also be useful for therapeutic selection, determining response to treatment, adjustment and dosing of treatment, monitoring ongoing therapeutic efficiency, and indication for change in therapeutic regimen.

In some embodiments of the present teachings, the biomarker panels and formulas can be used to aid in the diagnosis of inflammatory disease, and in the determination of the severity of inflammatory disease. The biomarker panels and formulas can also be used for determining the future status of intervention such as, for example in axSpA, determining the prognosis of future spine or sacroiliac joint erosion with or without treatment. Certain embodiments of the present teachings can be tailored to a specific treatment or a combination of treatments. X-ray is currently considered the gold standard for assessment of disease progression, but it has limited capabilities since subjects may have long periods of active symptomatic disease while radiographs remain normal or show only nonspecific changes. Conversely, subjects who seem to have quiescent disease (subclinical disease) may continue to progress over time, undetected clinically until significant radiographic damage has occurred. If subjects with a high likelihood of disease progression could be identified in advance, the opportunity for early aggressive treatment could result in much more effective disease outcomes. In certain embodiments of the present teachings, an algorithm developed from the biomarkers can be used, with significant power, to characterize the level of bone or cartilage damage activity in axSpA subjects. In other embodiments, an algorithm developed from the set of biomarkers can be used, with significant power, to prognose spinal or sacroiliac joint destruction over time. In other embodiments, the MBDA score can be used as a strong predictor of radiographic or other imaging-based progression, giving the clinician a novel way to identify subjects at risk of axSpA-induced joint damage and allowing for early prescription of spinal or sacroiliac joint-sparing agents, prophylactically.

In some embodiments of the present teachings, the biomarker panels and formulas can be used as surrogate markers of clinical events necessary for the development of inflammatory disease-specific agents; e.g., pharmaceutical agents. That is, the MBDA surrogate marker, derived from a biomarker panel, can be used in the place of clinical events in a clinical trial for an experimental axSpA treatment. Biomarker panels and formulas can thus be used to derive an inflammatory disease surrogate endpoint to assist in the design of experimental treatments for axSpA.

Measurement of Biomarkers

The quantity of one or more biomarkers of the present teachings can be indicated as a value. The value can be one or more numerical values resulting from the evaluation of a sample, and can be derived, e.g., by measuring level(s) of the biomarker(s) in a sample by an assay performed in a laboratory, or from dataset obtained from a provider such as a laboratory, or from a dataset stored on, e.g., a server. Levels of any particular biomarker can be measured using any of several techniques known in the art for that specific biomarker and assays for individual biomarkers can be combined into panel assays as disclosed herein. The present teachings encompass such techniques, and further include all subject fasting and/or temporal-based sampling procedures for measuring biomarkers.

The actual measurement of levels of a biomarker can be determined at the protein or nucleic acid level using any suitable method known in the art for that biomarker. "Protein" detection comprises detection of full-length proteins, mature proteins, pre-proteins, polypeptides, isoforms, mutations, variants, post-translationally modified proteins and variants thereof, and can be detected in any suitable manner. Levels of biomarkers can be determined at the protein level, e.g., by measuring the serum levels of peptides encoded by the gene products described herein, or by measuring the enzymatic activities of these protein biomarkers. Such methods are well-known in the art for individual biomarkers and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Expression of a biomarker can be detected and measured using techniques well-known to those of skill in the art for that biomarker (e.g., using sequence information provided by public database entries for the biomarker). For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

As an example, Northern hybridization analysis using probes which specifically recognize one or more of these sequences can be used to determine gene expression. Alternatively, expression can be measured using RT-PCR; e.g., polynucleotide primers specific for the differentially expressed biomarker mRNA sequences reverse-transcribe the mRNA into DNA, which is then amplified in PCR and can be visualized and quantified. Biomarker RNA can also be quantified using, for example, other target amplification methods, such as TMA, SDA, and NASBA, or signal amplification methods (e.g., bDNA), and the like. Ribonuclease protection assays can also be used, using probes that specifically recognize one or more biomarker mRNA sequences, to determine gene expression.

Alternatively, biomarker protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. See WO 04/056456 and WO 04/088309, each of which is hereby incorporated by reference in its entirety. In this regard, other biomarker analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other biomarker metabolites can be similarly detected using reagents that are specifically designed or tailored to detect such metabolites.

In some embodiments, a biomarker can be detected by contacting a subject sample with reagents, generating complexes of reagent and analyte, and detecting the complexes. Examples of "reagents" include but are not limited to nucleic acid primers and antibodies.

In some embodiments of the present teachings an antibody binding assay is used to detect a biomarker; e.g., a sample from the subject is contacted with an antibody reagent that binds the biomarker analyte, a reaction product (or complex) comprising the antibody reagent and analyte is generated, and the presence (or absence) or amount of the complex is determined. The antibody reagent useful in detecting biomarker analytes can be monoclonal, polyclonal, chimeric, recombinant, or a fragment of the foregoing, as discussed in detail above, and the step of detecting the reaction product can be carried out with any suitable immunoassay. The sample from the subject is typically a biological fluid as described above, and can be the same sample of biological fluid as is used to conduct the method described above.

Immunoassays carried out in accordance with the present teachings can be homogeneous assays or heterogeneous assays. In a homogeneous assay the immunological reaction can involve the specific antibody (e.g., anti-biomarker protein antibody), a labeled analyte, and the sample of interest. The label produces a signal, and the signal arising from the label becomes modified, directly or indirectly, upon binding of the labeled analyte to the antibody. Both the immunological reaction of binding, and detection of the extent of binding, can be carried out in a homogeneous solution. Immunochemical labels which can be employed include but are not limited to free radicals, radioisotopes, fluorescent dyes, enzymes, bacteriophages, and coenzymes. Immunoassays include competition assays.

In a heterogeneous assay approach, the reagents can be the sample of interest, an antibody, and a reagent for producing a detectable signal. Samples as described above can be used. The antibody can be immobilized on a support, such as a bead (such as protein A and protein G agarose beads), plate or slide, and contacted with the sample suspected of containing the biomarker in liquid phase. The support is separated from the liquid phase, and either the support phase or the liquid phase is examined using methods known in the art for detecting signal. The signal is related to the presence of the analyte in the sample. Methods for producing a detectable signal include but are not limited to the use of radioactive labels, fluorescent labels, or enzyme labels. For example, if the antigen to be detected contains a second binding site, an antibody which binds to that site can be conjugated to a detectable (signal-generating) group and added to the liquid phase reaction solution before the separation step. The presence of the detectable group on the solid support indicates the presence of the biomarker in the test sample. Examples of suitable immunoassays include but are not limited to oligonucleotides, immunoblotting, immunoprecipitation, immunofluorescence methods, chemiluminescence methods, electrochemiluminescence (ECL), and/ or enzyme-linked immunoassays (ELISA).

Those skilled in the art will be familiar with numerous specific immunoassay formats and variations thereof which can be useful for carrying out the method disclosed herein. See, e.g., E. Maggio, *Enzyme-Immunoassay* (1980), CRC Press, Inc., Boca Raton, Fla. See also U.S. Pat. No. 4,727, 022 to C. Skold et al., titled "Novel Methods for Modulating Ligand-Receptor Interactions and their Application"; U.S. Pat. No. 4,659,678 to G C Forrest et al., titled "Immunoassay of Antigens"; U.S. Pat. No. 4,376,110 to G S David et al., titled "Immunometric Assays Using Monoclonal Antibodies"; U.S. Pat. No. 4,275,149 to D. Litman et al., titled "Macromolecular Environment Control in Specific Receptor Assays"; U.S. Pat. No. 4,233,402 to E. Maggio et al., titled "Reagents and Method Employing Channeling"; and, U.S. Pat. No. 4,230,797 to R. Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein can likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies may also be useful for detecting post-translational modifications of biomarkers. Examples of post-translational modifications include, but are not limited to tyrosine phosphorylation, threonine phosphorylation, serine phosphorylation, citrullination and glycosylation (e.g., O-GlcNAc). Such antibodies specifically detect the phosphorylated amino acids in a protein or proteins of interest, and can be used in the immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF). See U. Wirth et al., *Proteomics* 2002, 2(10): 1445-1451.

Reports

In some embodiments, a report is prepared in a format that is capable of being disseminated to the subject or a caregiver of the subject that provides information allow the subject or caregiver to make decisions based on the diagnosis Kits Other embodiments of the present teachings comprise biomarker detection reagents packaged together in the form of a kit for conducting any of the assays of the present teachings. In certain embodiments, the kits comprise oligonucleotides that specifically identify one or more biomarker nucleic acids based on homology and/or complementarity with biomarker nucleic acids. The oligonucleotide sequences may correspond to fragments of the biomarker nucleic acids. For example, the oligonucleotides can be more than 200, 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a MBDA score, can be included in the kit; e.g., written, tape, VCR, or CD-ROM. The assay can for example be in the form of a Northern hybridization or a sandwich ELISA as known in the art.

In some embodiments of the present teachings, biomarker detection reagents can be immobilized on a solid matrix, such as a porous strip, to form at least one biomarker detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of biomarker present in the sample. The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. The nucleic acids on the array specifically identify one or more nucleic acid sequences represented by the biomarkers. In various embodiments, the expression of one or more of the sequences represented by the biomarkers can be identified by virtue of binding to the array. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Machine-Readable Storage Medium

A machine-readable storage medium can comprise, for example, a data storage material that is encoded with machine-readable data or data arrays. The data and machine-readable storage medium are capable of being used for a variety of purposes, when using a machine programmed with instructions for using said data. Such purposes include, without limitation, storing, accessing and manipulating information relating to the inflammatory disease activity of a subject or population over time, or disease activity in response to inflammatory disease treatment, or for drug discovery for inflammatory disease, etc. Data comprising measurements of the biomarkers of the present teachings, and/or the evaluation of disease activity or disease state from these biomarkers, can be implemented in computer programs that are executing on programmable computers, which comprise a processor, a data storage system, one or more input devices, one or more output devices, etc. Program code can be applied to the input data to perform the functions described herein, and to generate output information. This output information can then be applied to one or more output devices, according to methods well-known in the art. The computer can be, for example, a personal computer, a microcomputer, or a workstation of conventional design.

The computer programs can be implemented in a high-level procedural or object-oriented programming language, to communicate with a computer system such as for example, the computer system illustrated in FIG. 12. The programs can also be implemented in machine or assembly language. The programming language can also be a compiled or interpreted language. Each computer program can be stored on storage media or a device such as ROM, magnetic diskette, etc., and can be readable by a programmable computer for configuring and operating the computer when the storage media or device is read by the computer to perform the described procedures. Any health-related data management systems of the present teachings can be considered to be implemented as a computer-readable storage medium, configured with a computer program, where the storage medium causes a computer to operate in a specific manner to perform various functions, as described herein.

The biomarkers disclosed herein can be used to generate a "subject biomarker profile" taken from subjects who have inflammatory disease. The subject biomarker profiles can then be compared to a reference biomarker profile, in order to diagnose or identify subjects with inflammatory disease, to monitor the progression or rate of progression of inflammatory disease, or to monitor the effectiveness of treatment for inflammatory disease. The biomarker profiles, reference and subject, of embodiments of the present teachings can be contained in a machine-readable medium, such as analog tapes like those readable by a CD-ROM or USB flash media, among others. Such machine-readable media can also contain additional test results, such as measurements of clinical parameters and clinical assessments. The machine-readable media can also comprise subject information; e.g., the subject's medical or family history. The machine-readable media can also contain information relating to other disease activity algorithms and computed scores or indices, such as those described herein.

EXAMPLES

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, *Proteins: Structures and Molecular Properties,* 1993, W. Freeman and Co.; A. Lehninger, *Biochemistry,* Worth Publishers, Inc. (current addition); J. Sambrook et al., *Molecular Cloning: A Laboratory Manual,* 2nd Edition, 1989; *Methods In Enzymology,* S. Colowick and N. Kaplan, eds., Academic Press, Inc.; *Remington's Pharmaceutical Sciences,* 18th Edition, 1990, Mack Publishing Company, Easton, Pa.; Carey and Sundberg, *Advanced Organic Chemistry, Vols. A and B,* 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, *Statistical Analysis with Missing Data,* 2nd Edition 2002, John Wiley and Sons, Inc., NJ; M. Pepe, *The Statistical Evaluation of Medical Tests for Classification and Prediction* (*Oxford Statistical Science Series*) 2003, Oxford University Press, Oxford, UK; X. Zhoue et al., *Statistical Methods in Diagnostic Medicine* 2002, John Wiley and Sons, Inc., NJ; T. Hastie et. al, *The Elements of Statistical Learning: Data Mining, Inference, and Prediction,* Second Edition 2009, Springer, N.Y.; W. Cooley and P. Lohnes, *Multivariate procedures for the behavioral science* 1962, John Wiley and Sons, Inc. NY; E. Jackson, *A User's Guide to Principal Components* 2003, John Wiley and Sons, Inc., NY.

Example 1

Identification of Serum Protein Biomarkers Associated with AS

Candidate biomarkers were evaluated for association with the Ankylosing Spondylitis Disease Activity Score (AS-DAS) using either ESR or CRP as the acute inflammatory marker, or the modified Stoke Ankylosing Spondylitis Spinal Score (mSASSS). The first set of candidate markers includes the 12 biomarkers of the VECTRA® DA test: vascular cell adhesion molecule-1 (VCAM-1), epidermal growth factor (EGF), vascular endothelial growth factor A (VEGF-A), Interleukin 6 (IL-6), tumor necrosis factor receptor, type 1 (TNF-R1), matrix metalloproteinase-1 (MMP-1), matrix metalloproteinase-3 (MMP-3), YKL-40, Leptin, Resistin, serum amyloid (SAA), and C-reactive protein (CRP). The VECTRA® DA biomarkers are described in detail in U.S. patent application Ser. No. 12/905,984, which is hereby incorporated by reference in its entirety. In brief, the VECTRA® DA multi-biomarker assay measures levels of the 12 biomarkers and uses a pre-specified algorithm to generate a multi-biomarker disease activity score (MBDA score) ranging from 1-100. The MBDA score has demonstrated strong correlations with rheumatoid arthritis (RA) clinical disease activity in multiple cohorts (Bakker et al. *Annals of the Rheumatic Diseases* 71:1692-7 (2012); Curtis et al. *arthritis care & research* 64:1794-803 (2012)).

The candidate biomarkers further includes each biomarker included in the DA-17 panel of biomarkers. The DA-17 biomarkers include the VECTRA® DA biomarkers described above in addition to Macrophage-derived chemokine (MDC), interleukin-6 receptor (IL-6R), intercellular adhesion molecule 1 (ICAM-1), interleukin-8 (IL-8), and interleukin-1 beta (IL-1B), and calprotectin. The DA-17 biomarkers are listed in Table A.

TABLE A

| Symbol | Full name | NCBI RefSeq |
|---|---|---|
| VCAM-1 | Vascular cell adhesion molecule-1 | NP_001069.1 |
| EGF | Epidermal growth factor | NP_001954.2 |
| VEGF-A | Vascular endothelial growth factor A | NP_001020539.2 |
| IL-6 | Interleukin-6 | NP_000591.1 |
| TNF-R1 | Tumor necrosis factor receptor, type 1 | NP_001056.1 |
| MMP-1 | Matrix metalloproteinase-1 | NP_002412.1 |
| MMP-3 | Matrix metalloproteinase-3 | NP_002413.1 |
| YKL-40 | Chitinase 3-like 1 | NP_001267.2 |
| Leptin | Leptin | NP_000221.1 |
| Resistin | Resistin | NP_065148.1 |
| SAA | Serum amyloid | NP_000322.2 |
| CRP | C-reactive protein | NP_000558.2 |
| MDC | Macrophage-derived chemokine | NP_002981.2 |
| IL-6R | Interleukin 6 receptor | NP_000556.1 |
| ICAM-1 | Intercellular adhesion molecule 1 | NP_001069.1 |
| IL-8 | Interleukin-8 | NP_000575.1 |
| IL-1B | Interleukin-1 beta | NP_000567.1 |
| S100A8 | Calprotectin | NP_002955.2 |
| S100A9 | Calprotectin | NP_002956.1 |

Serum samples were obtained at the point of care and at the time of routine clinical blood draws from forty individuals. Table C summarizes the clinical characteristics of the cohort.

TABLE C

| | |
|---|---|
| Total Number (N) | 40 |
| Age, Mean (Range) | 43 |
| | (20-66) |
| Female (n) | 14 |
| Male (n) | 26 |

TABLE C-continued

| | |
|---|---|
| HLAB27 (+) | 30 |
| CRP range | 0.04-7 mg/dL |
| CRP mean | 1.9 mg/dL |
| CRP median | 1.5 mg/dL |

All biomarker assays were performed at controlled ambient temperature of 20±5° C. Multispot 96-well plates (MSD) were spotted in specific locations with biomarker-specific capture antibodies for. Biomarker concentrations were determined using 3 separate multiplex panels, based on sample dilution requirements. Prediluted standards and QC run controls were loaded onto the plate alongside diluted patient samples and diluted process controls. Diluted serum samples and process controls were prepared using a validated Hamilton STAR (Reno, Nev., USA) automated dilution platform.

The VECTRA® DA biomarkers were assayed to determine measurability. To establish the assay's dynamic range for each biomarker, the limit of quantitation (LOQ), defined as the actual amount of analyte that can be reliably detected in a sample and at which the total analytical error meets the requirements for accuracy and precision, was determined as described in EP17-A Clinical Laboratory Standards Institute (CLSI). Acceptable accuracy at the LOQ was defined as 80-120% recovery of the input mass based on the vendor's specification for each particular protein, and the acceptable precision requirement at the LOQ was defined as a 20% CV. An assay's analytical measurable range was defined as the difference between the upper limit (ULOQ) and the lower limit (LLOQ). The clinically reportable or dynamic range for an assay was defined as the dilution-adjusted range. Non-VECTRA® DA biomarkers were analyzed via commercially available standard ELISAs.

Univariate Analysis

Figure 2:
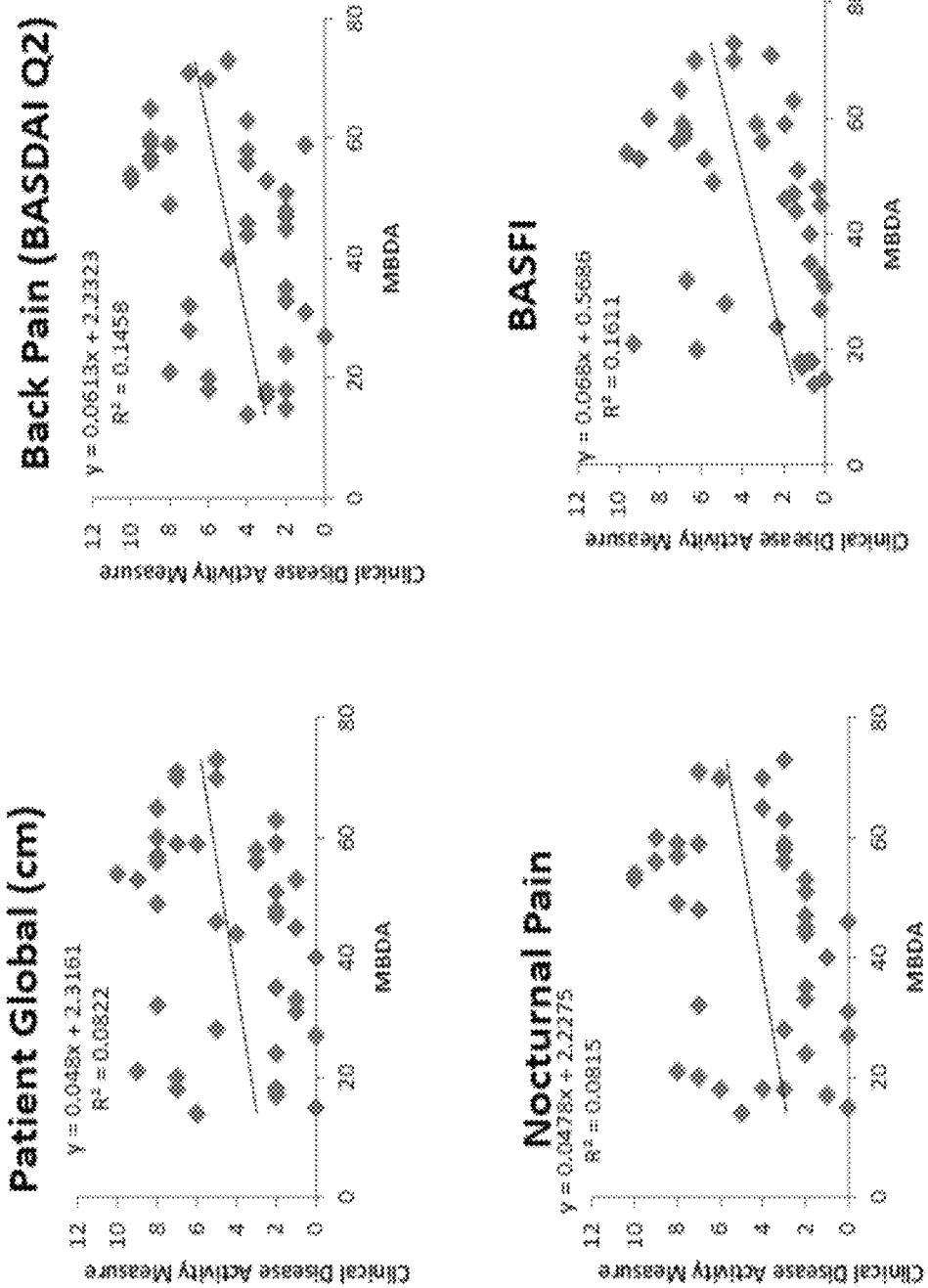
FIG. 2 illustrates the 12 biomarker VECTRA® DA panel MBDA comparisons with components of other measures of disease status, Patient Global from ASDAS (upper left), Back Pain from BASDAI (upper right), nocturnal pain from BASFI (lower left), and BASFI itself (lower right).

For intra-run precision of an MBDA score, 4 serum pools were each run 14 times on a single plate. Two plates from each of 2 different lots were evaluated, and the means and % CVs for the MBDA score were calculated. Associations were calculated between the MBDA scores and ASDAS-ESR, ASDAS-CRP, and mSASSS (see FIGS. 1, 3, and 4, and Table ZZ of U.S. provisional patent applications 62/010,252 and 62/078,667, both of which are incorporated herein by reference). Associations were further calculated between the MBDA scores and the patient global, back pain, nocturnal pain, and BASFI assessments (FIG. 2).

The most informative biomarkers for overall assessment of AS disease activity were then chosen. An importance score was generated for each biomarker through an array of univariate and multivariate analyses. Univariate analysis was performed to evaluate the correlation between each individual biomarker and each clinical measure.

Assessment Scoring

Samples acquired from the cohorts described above were analyzed using the selected biomarkers. The Ankylosing Spondylitis Disease Activity Score (ASDAS) and mSASSS scores were calculated for each sample.

Strong correlations were observed between the 12 biomarker VECTRA® DA MBDA panel and the ASDAS (ESR and CRP) scores (FIG. 1). Strong correlations were further observed between the 12 biomarker VECTRA® DA MBDA panel and other clinical assessment standards such as mSASSS and BASDAI (FIG. 1); and patient global, back pain, nocturnal pain, and BASFI (FIG. 2). FIGS. 3 and 4 illustrate individual biomarker comparisons with ASDAS-ESR, ASDAS-CRP, and mSASSS based on Pearson Correlation Coefficients and secondary algorithms, respectfully.

Figure 5:
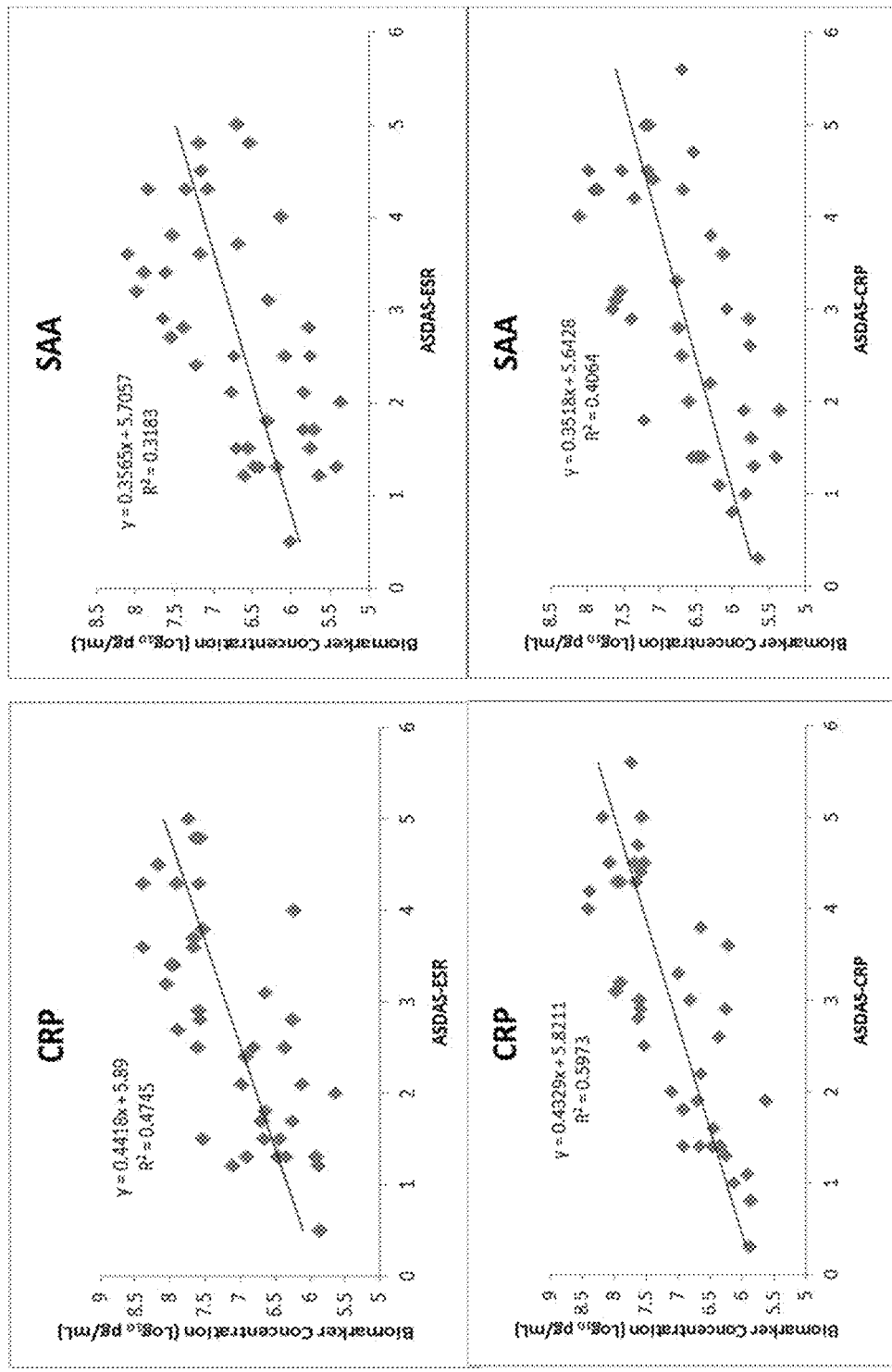
FIG. 5 illustrates a graphical representation of the individual biomarker s CRP (left) and SAA (right) with ASDAS-ESR and ASDAS-CRP.
Figure 6:
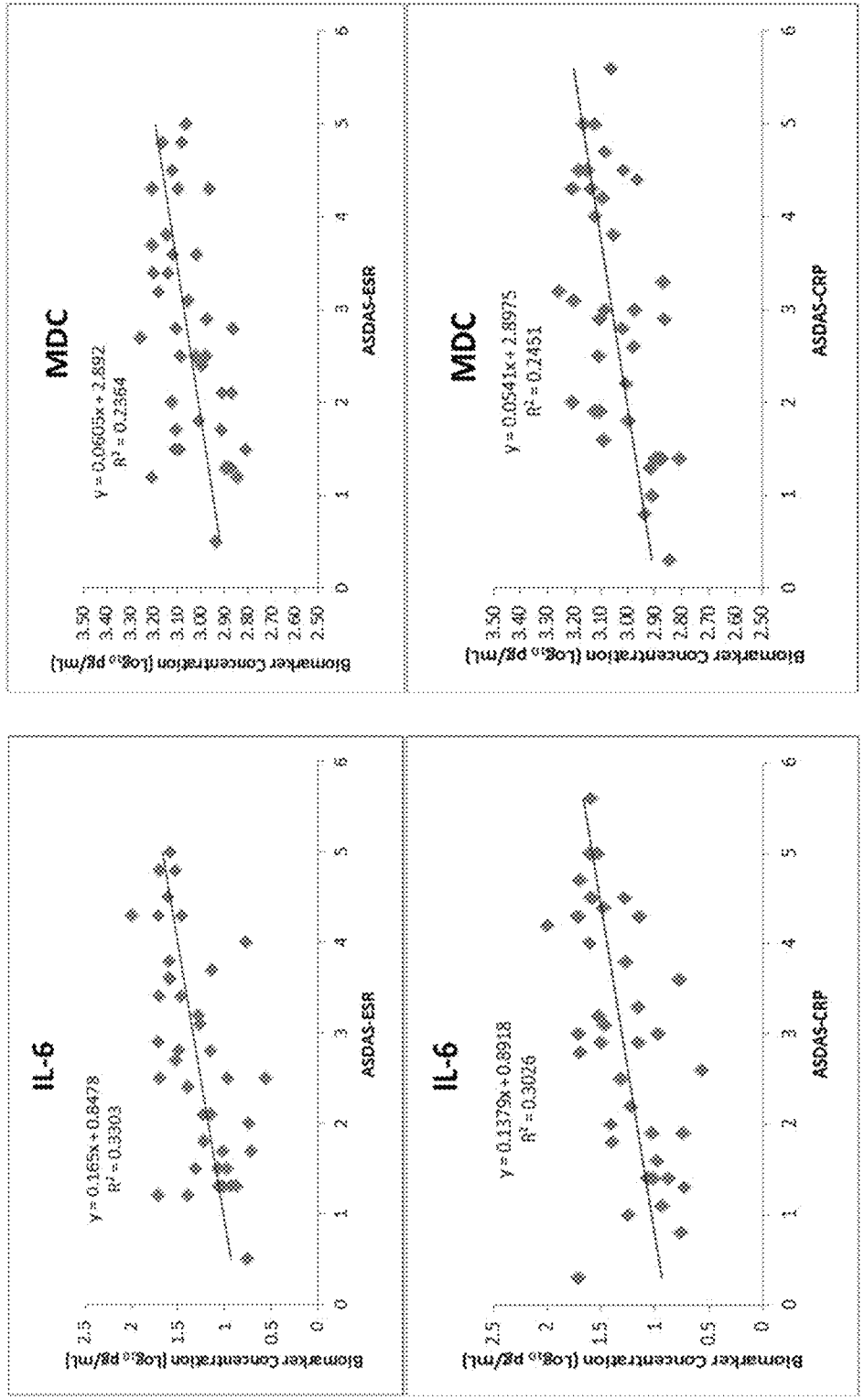
FIG. 6 illustrates a graphical representation of the individual biomarker s IL-6 (left) and MDC (right) with ASDAS-ESR and ASDAS-CRP.
Figure 7:
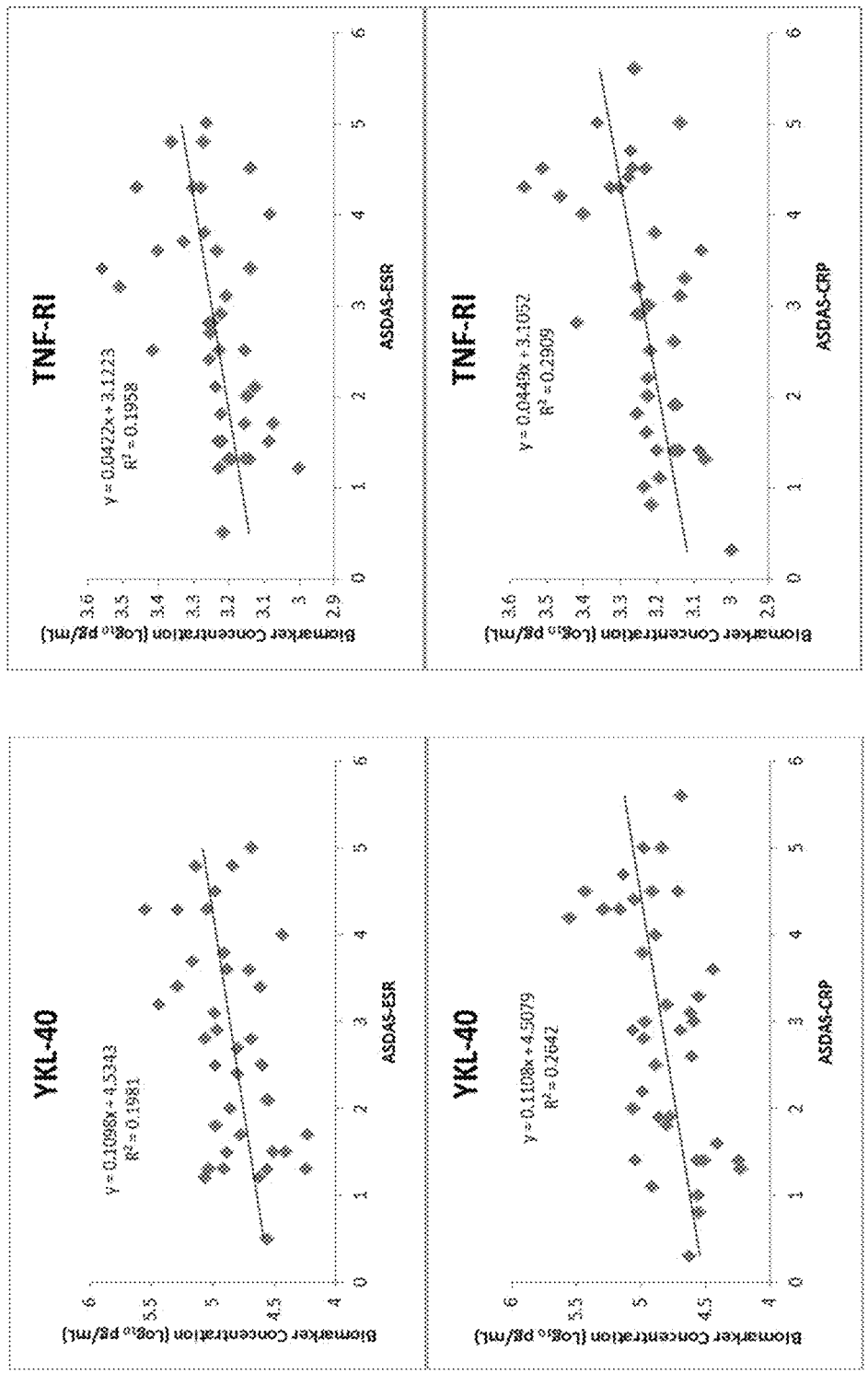
FIG. 7 illustrates a graphical representation of the individual biomarker s YK-40 (left) and TNF-R1 (right) with ASDAS-ESR and ASDAS-CRP.

FIGS. 5-7 illustrate the correlations of selected individual biomarker to ASDAS-ESR, ASDAS-CRP, and mSASSS.

Figure 11:
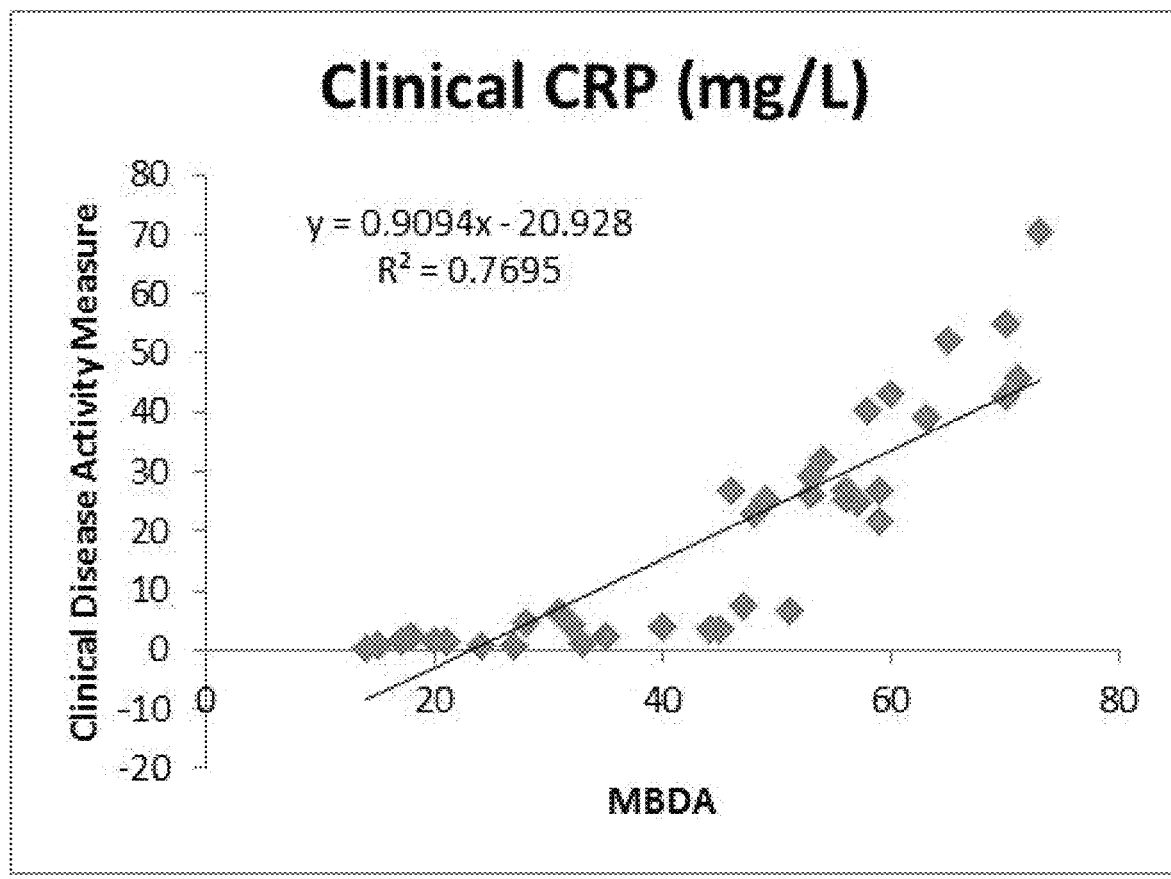
FIG. 11 illustrates a graphical representation of the MBDA score against CRP.

FIG. 10 provides a table of Pearson correlation coefficients that are sorted based on ASDAS-ESR and further illustrates additional individual biomarker comparisons with ASDAS-CRP, mSASSS, BASDAI, and BASFI. FIG. 10 demonstrates that specific biomarkers correlate different based on the clinical assessment that they are compared to. For example, MDC correlates stronger with ASDAS than mSASSS. This allows for development of multi-partite algorithms having different components that correlate with different clinical assessments that represent different disease attributes, such as inflammatory and structural damage, which can then be combined for an overall score. FIG. 11 demonstrates that the MBDA test is a better predictor of disease activity than CRP, because the MBDA test can detect disease activity in AS patients having low CRP.

Figure 8:
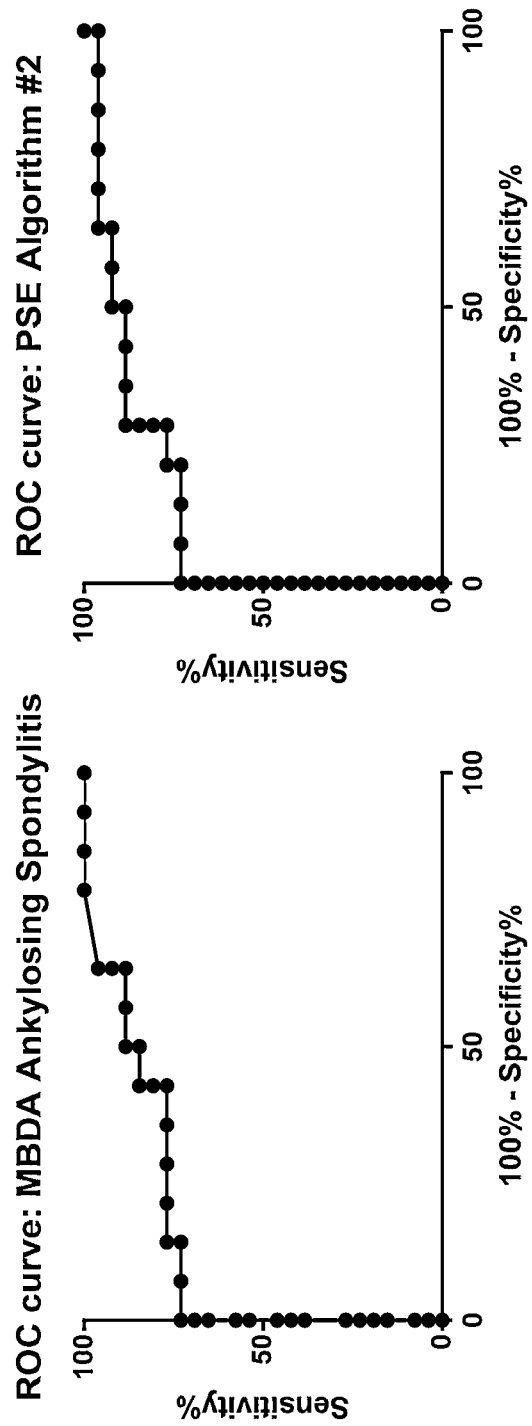
FIG. 8 illustrates the AUROC using the VECTRA® DA panel for active AS with two different algorithms.
Figure 9:
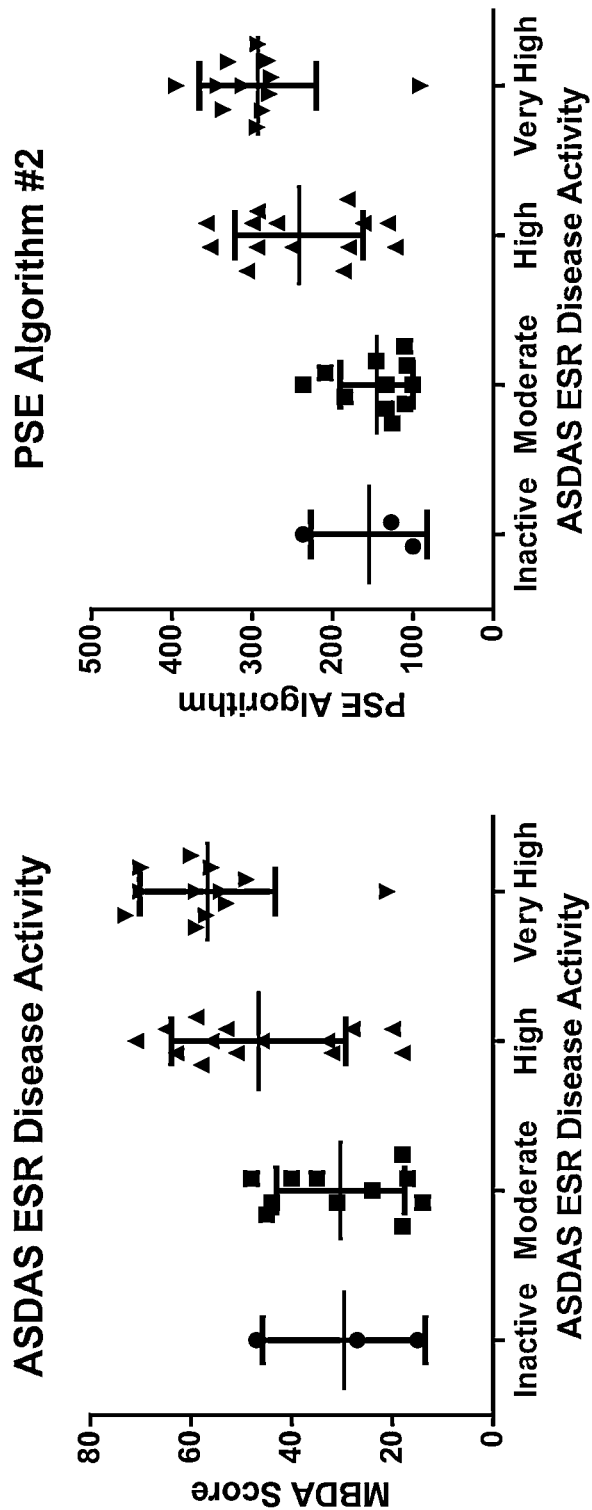
FIG. 9 compares second algorithm against MBDA score discriminating different levels of disease activity.

The performance of the biomarkers was further evaluated by determining AUROC. Use of two algorithms showed the MBDA panel to have an AUROC of 0.87 (P value 0.0001643) and 0.88 (P value 0.0001037) (FIG. 8). Finally, an algorithm based on centration percentiles and correlation coefficients outperforms MBDA alone (FIG. 9).

What is claimed is:

1. A method for treating axial spondyloarthritis (axSpA) disease activity in a subject, the method comprising:
    providing a test sample comprising bodily fluid taken from the subject;
    determining in the sample concentrations of biomarkers comprising chitinase 3-like 1 (cartilage glycoprotein-39) (CHI3L1, or YKL-40); C-reactive protein, pentraxin-related (CRP); epidermal growth factor (beta-urogastrone) (EGF); interleukin 6 (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA);
    determining from the sample biomarker concentrations of chitinase 3-like 1 (cartilage glycoprotein-39) (CHI3L1, or YKL-40); C-reactive protein, pentraxin-related (CRP); epidermal growth factor (beta-urogastrone) (EGF); interleukin 6 (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A or TNF-R1); vascular cell adhesion molecule 1 (VCAM1); and vascular endothelial growth factor A (VEGFA) a biomarker axSpA disease activity score with one or more statistical tools to provide an interpretation function;
    classifying disease activity of axSpA in the subject based on the axSpA disease activity score, wherein the classification indicates a need for a therapy for axSpA; and
    administering a therapy for axSpA to the subject in need thereof comprising one or more of DMARD therapy, bariatric surgery, and administration of a therapeutic compound.

2. The method of claim 1, wherein the therapeutic compound is selected from an NSAID, a corticosteroid, a JAK inhibitor, a TNF inhibitor, an IL1 inhibitor, a T-cell modulator, a B-cell modulator, and an IL6 inhibitor.

3. The method of claim 1 wherein the therapeutic compound is selected from MTX, azathioprine (AZA), bucillamine (BUC), chloroquine (CQ), ciclosporin, doxycycline (DOXY), hydroxychloroquine (HCQ), intramuscular gold (IM gold), leflunomide (LEF), levofloxacin (LEV), sulfasalazine (SSZ), certolizumab, apremilast, folinic acid, D-penicillamine, gold auranofin, gold aurothioglucose, gold thiomalate, cyclophosphamide, chlorambucil, infliximab, adalimumab, etanercept, golimumab, anakinra, abatacept, rituximab, and tocilizumab.

4. The method of claim 1, further comprising determining the interpretation function by applying the statistical tools to the sample biomarker concentrations along with a clinical assessment of the subject to provide the axSpA disease activity score, wherein the clinical assessment is one or more of Ankylosing Spondylitis Disease Activity Score (ASDAS), the Stoke Ankylosing Spondylitis Spinal Score (SASSS); the modified Stoke Ankylosing Spondylitis Spinal Score (mSASSS); Ankylosing Spondylitis Quality of Life Scale (ASQOL); Bath Ankylosing Spondylitis Disease Activity Index (BASDAI), Bath Ankylosing Spondylitis Functional Index (BASFI), Bath Ankylosing Spondylitis Global Score (BAS-G), Bath Ankylosing Spondylitis Metrology Index (BASMI), Dougados Functional Index (DFI), Health Assessment Questionnaire for the Spondyloarthropathies (HAQ-S), Revised Leeds Disability Questionnaire (RLDQ), and MRI.

5. The method of claim 1, wherein the subject has previously received a treatment for axSpA, and further monitoring efficacy of the treatment based on the biomarker axSpA score.

6. The method of claim 1 wherein a report is prepared in a format that is capable of being disseminated to the subject or a caregiver of the subject that provides information allowing the subject or caregiver to make decisions based on the diagnosis.

7. The method of claim 1, wherein the axSpA is nr-axSpA (non-radiographic axial spondyloarthritis) or ankylosing spondylitis (AS).

8. The method of claim 1, further comprising monitoring progressive damage to a spine or sacroiliac joint of the subject based on the axSpA disease activity score.

9. The method of claim 1, wherein the subject has CRP below 10 mg/L.

10. The method of claim 1, further comprising determining in the sample concentrations of biomarkers calprotectin (dimer of S100A8 and S100A9 protein subunits; MRP-8/14); intercellular adhesion molecule 1 (ICAM1); interleukin 8 (IL8); interleukin 1, beta (IL1B); interleukin 6 receptor (IL6R); Macrophage-derived chemokine (MDC).

11. The method of claim 1, further comprising monitoring axial spondyloarthritis (axSpA) disease activity in the subject.

12. The method of claim 1, further comprising diagnosing axSpA in the subject.

13. The method of claim 1, further comprising predicting risk of progressive damage in axSpA in the subject.

* * * * *